US012752038B2

(12) United States Patent
Mueller

(10) Patent No.: US 12,752,038 B2
(45) **Date of Patent: *Oct. 6, 2026**

(54) SYNERGISTIC ACTIVITY OF NOVEL COMPOUNDS AGAINST PLANKTONIC AND BIOFILM CELLS OF CLINICALLY RELEVANT PATHOGENS

(71) Applicant: SterileCare Inc., Markham (CA)

(72) Inventor: Karen Mueller, Newmarket (CA)

(73) Assignee: SterileCare Inc., Markham, CA (US)

( * ) Notice: Subject to any disclaimer, the term of this patent is extended or adjusted under 35 U.S.C. 154(b) by 385 days.

This patent is subject to a terminal disclaimer.

Patent file contains an affidavit/declaration under 37 CFR 1.130(b).

(21) Appl. No.: 17/874,526

(22) Filed: Jul. 27, 2022

(65) Prior Publication Data

US 2023/0046081 A1 Feb. 16, 2023

Related U.S. Application Data

(60) Provisional application No. 63/226,109, filed on Jul. 27, 2021.

(30) Foreign Application Priority Data

Jul. 26, 2022 (TW) ................................. 111128029

(51) Int. Cl.

*A61L 24/00* (2006.01)
*A61K 31/155* (2006.01)
*A61K 31/198* (2006.01)
*A61L 29/16* (2006.01)

(52) U.S. Cl.

CPC ........ *A61L 24/0015* (2013.01); *A61K 31/155* (2013.01); *A61K 31/198* (2013.01); *A61L 29/16* (2013.01); *A61L 2300/206* (2013.01); *A61L 2300/404* (2013.01)

(58) Field of Classification Search

CPC ..... A61K 31/198; A61K 31/045; A61P 31/00; A61P 31/04; A61L 2300/206; A61L 2300/404; A61L 24/0015

See application file for complete search history.

(56) References Cited

U.S. PATENT DOCUMENTS

| | | | |
|---|---|---|---|
| 2,474,412 | A | 6/1949 | Bersworth |
| 3,962,109 | A | 6/1976 | Oberhofer et al. |
| 4,258,056 | A | 3/1981 | Lentsch |
| 4,307,109 | A | 12/1981 | Arbir et al. |
| 4,847,004 | A | 7/1989 | McLeod |
| 5,180,749 | A | 1/1993 | Cusack et al. |
| 5,362,754 | A | 11/1994 | Raad et al. |
| 5,688,516 | A | 11/1997 | Raad et al. |
| 5,708,023 | A | 1/1998 | Modak et al. |
| 5,731,356 | A | 3/1998 | Jones et al. |
| 5,800,827 | A | 9/1998 | Igarashi et al. |
| 5,820,607 | A | 10/1998 | Tcholakian et al. |
| 5,908,869 | A | 6/1999 | Jones et al. |
| 5,910,420 | A | 6/1999 | Tuompo et al. |
| 6,004,539 | A | 12/1999 | Longo, Jr. et al. |
| 6,126,706 | A | 10/2000 | Matsumoto et al. |
| 6,165,484 | A | 12/2000 | Raad et al. |
| 6,166,007 | A | 12/2000 | Sodemann |
| 6,187,768 | B1 | 2/2001 | Welle et al. |
| 6,197,738 | B1 | 3/2001 | Regutti |
| 6,267,979 | B1 | 7/2001 | Raad et al. |
| 6,350,251 | B1 | 2/2002 | Prosl et al. |
| 6,423,706 | B2 | 7/2002 | Sodemann |
| 6,429,225 | B1 | 8/2002 | Nagai et al. |
| 6,498,157 | B2 | 12/2002 | Sodemann |
| 6,500,861 | B1 | 12/2002 | Wider |
| 6,509,319 | B1 | 1/2003 | Raad et al. |
| 6,569,852 | B1 | 5/2003 | Sodemann |
| 6,583,181 | B1 | 6/2003 | Chiang et al. |
| 6,592,564 | B2 | 7/2003 | Finch et al. |
| 6,679,870 | B1 | 1/2004 | Finch et al. |
| 6,727,210 | B1 | 4/2004 | Perdew |
| 6,762,160 | B2 | 7/2004 | Barbeau et al. |
| 8,541,472 | B2 | 9/2013 | Kite et al. |

(Continued)

FOREIGN PATENT DOCUMENTS

| | | |
|---|---|---|
| AE | P2024-02186 | 8/2024 |
| AE | P2024-02191 | 8/2024 |

(Continued)

OTHER PUBLICATIONS

Aschenbeck et al., "Allergenic Ingredients in Personal Hygiene Wet Wipes" Dermatitis, Oct. 2017, vol. 28(5), pp. 317-323.
Banin et al., "Chelator-induced dispersal and killing of Pseudomonas aeruginosa cells in a biofilm", Applied and Environmental Microbiology, 2006, 72(3), pp. 2064-2069.
Beasley et al., "Preservatives in nebulizer solutions: Risks without benefit", Pharmacotherapy, 1998, 18(1), pp. 130-139.
Brown et al., "Edetate Sodium Aerosol in Psuedomonas Lung Infection in Cystic Fibrosis", American Journal of Diseases in Children, 1985, vol. 139(8), pp. 836-839.
Cashman, "Why the lower reported prevalence of asthma in patients diagnosed with COVID-19 validates repurposing EDTA solutions to prevent and manage treat COVID-19 disease", Medical Hypothesis, 2020, 144, 110027.

(Continued)

*Primary Examiner* — Anna R Falkowitz
*Assistant Examiner* — John P Nguyen
(74) *Attorney, Agent, or Firm* — Polsinelli LLP

(57) ABSTRACT

The present disclosure provides compositions, methods of preparing, and method of use of a composition comprising: (a) about 0.05 wt % to about 10.0 wt % ethylenediamaminetetraacetic acid, a salt thereof, a chelating agent, or a combination thereof; (b) from about 2.0 wt % to 50.0 wt % ethanol (ET), isopropyl alcohol (IPA), or a combination thereof; and (c) from about 0.015 μg/mL to about 100.0 μg/mL chlorhexidine, a salt thereof, or a combination thereof. These compositions, as disclosed herein, eliminate greater the 95% of planktonic or biofilm cells from a central venous access device.

21 Claims, 5 Drawing Sheets

(56) References Cited

U.S. PATENT DOCUMENTS

| | | | |
|---|---|---|---|
| 8,703,053 B2 | 4/2014 | Kite et al. | |
| 8,703,828 B2 | 4/2014 | Ash et al. | |
| 8,828,317 B2 | 9/2014 | Kite et al. | |
| 8,911,665 B2 | 12/2014 | Kite et al. | |
| 9,078,441 B2 | 7/2015 | Raad | |
| 9,155,720 B2 | 10/2015 | Kite et al. | |
| 9,408,933 B2 | 8/2016 | Kite et al. | |
| 10,046,156 B2 | 8/2018 | Gardner | |
| 10,086,114 B2 | 10/2018 | Rosenblatt et al. | |
| 10,238,856 B2 | 3/2019 | Tennican | |
| 10,264,786 B2 | 4/2019 | Kite et al. | |
| 10,313,844 B2 | 6/2019 | Gupta et al. | |
| 10,524,982 B2 | 1/2020 | Fangrow | |
| 10,973,950 B2 | 4/2021 | Santerre et al. | |
| 11,351,353 B2 | 6/2022 | Ziebol et al. | |
| 11,400,195 B2 | 8/2022 | Ziebol et al. | |
| 11,944,776 B2 | 4/2024 | Ziebol et al. | |
| 2001/0003746 A1 | 6/2001 | Sodemann | |
| 2002/0010438 A1 | 1/2002 | Finch et al. | |
| 2002/0018732 A1 | 2/2002 | Hung et al. | |
| 2002/0098159 A1 | 7/2002 | Wei et al. | |
| 2002/0111346 A1 | 8/2002 | Sodemann | |
| 2002/0183216 A1 | 12/2002 | Koenig et al. | |
| 2003/0153983 A1 | 8/2003 | Miller et al. | |
| 2004/0047763 A1 | 3/2004 | Kite et al. | |
| 2005/0070989 A1 | 3/2005 | Lye et al. | |
| 2006/0121098 A1 | 6/2006 | Mendoza et al. | |
| 2007/0202177 A1 | 8/2007 | Hoang | |
| 2008/0194279 A1 | 8/2008 | Choksi et al. | |
| 2009/0099529 A1 | 4/2009 | Anderson et al. | |
| 2010/0055086 A1* | 3/2010 | Raad | A01N 37/44 514/56 |
| 2010/0087788 A1* | 4/2010 | Rosenblatt | A61L 29/16 422/28 |
| 2010/0256576 A1 | 10/2010 | Aggarwal et al. | |
| 2013/0136801 A1 | 5/2013 | Tennican | |
| 2013/0164363 A1 | 6/2013 | Raad | |
| 2013/0171030 A1 | 7/2013 | Ferlic et al. | |
| 2013/0338644 A1 | 12/2013 | Solomon et al. | |
| 2014/0142468 A1 | 5/2014 | Hossack et al. | |
| 2014/0322075 A1 | 10/2014 | Ferlic et al. | |
| 2017/0151373 A1 | 6/2017 | Rosenblatt et al. | |
| 2020/0139103 A1 | 5/2020 | Ziebol et al. | |
| 2021/0093791 A1 | 4/2021 | Anderson et al. | |
| 2021/0205596 A1 | 7/2021 | Ziebol et al. | |
| 2022/0339099 A1 | 10/2022 | Wring et al. | |
| 2023/0263757 A1 | 8/2023 | Mueller | |
| 2023/0263758 A1 | 8/2023 | Mueller | |
| 2023/0264009 A1 | 8/2023 | Mueller | |
| 2023/0302233 A1 | 9/2023 | Mueller | |
| 2025/0108004 A1 | 4/2025 | Mueller | |
| 2025/0108027 A1 | 4/2025 | Mueller | |

FOREIGN PATENT DOCUMENTS

| | | |
|---|---|---|
| AE | P2024-02193 | 8/2024 |
| AU | 2023006000 | 7/2024 |
| AU | 2023225210 | 7/2024 |
| AU | 2023226507 | 7/2024 |
| BR | 11 2024 015660 5 | 7/2024 |
| BR | 11 2024 017167 1 | 8/2024 |
| BR | 1120240171558 | 8/2024 |
| CA | 2856534 | 6/2013 |
| CN | 101627885 | 1/2010 |
| DE | 1944363 | 4/1970 |
| DE | 40 28 957 | 5/1994 |
| EP | 171122 | 2/1988 |
| EP | 0 836 917 | 4/1998 |
| EP | 1 238 677 | 9/2002 |
| EP | 23759406.4 | 8/2024 |
| EP | 23759407.2 | 8/2024 |
| EP | 23759408.0 | 8/2024 |
| EP | 4482537 | 1/2025 |
| EP | 4482538 | 1/2025 |
| EP | 4482544 | 1/2025 |
| FR | 2 780 283 | 12/1999 |
| GB | 1279148 | 6/1972 |
| GB | 2 292 888 | 3/1996 |
| HU | 201 247 | 10/1989 |
| JP | 62 153952 | 7/1987 |
| JP | 3 135518 | 6/1991 |
| KR | 10-2014-0097251 | 8/2014 |
| SA | 1120244720 | 8/2024 |
| SA | 1120244721 | 8/2024 |
| SA | 1120244722 | 8/2024 |
| TW | 202310827 | 3/2023 |
| WO | WO 94/10838 | 5/1994 |
| WO | WO 96/39215 | 12/1996 |
| WO | WO 98/50461 | 11/1998 |
| WO | WO 99/10017 | 3/1999 |
| WO | WO 00/03599 | 1/2000 |
| WO | WO 00/13656 | 3/2000 |
| WO | WO 00/27438 | 5/2000 |
| WO | WO 00/30460 | 6/2000 |
| WO | WO 01/37659 | 5/2001 |
| WO | WO 2002/24143 | 3/2002 |
| WO | WO 02/062260 | 8/2002 |
| WO | WO 02/072748 | 9/2002 |
| WO | WO 03/088914 | 10/2003 |
| WO | WO 2004/108093 | 12/2004 |
| WO | WO 2007/005720 | 1/2007 |
| WO | WO 2010/110908 | 9/2010 |
| WO | WO 2016/025775 | 2/2016 |
| WO | WO 2017/079589 | 5/2017 |
| WO | WO 2018/232453 | 12/2018 |
| WO | WO 2023/007399 | 2/2023 |
| WO | WO 2023/161827 | 8/2023 |
| WO | WO 2023/161828 | 8/2023 |
| WO | WO 2023/161829 | 8/2023 |
| WO | WO 2023/187622 | 10/2023 |
| WO | PCT/IB2024/059351 | 9/2024 |
| WO | PCT/IB2024/059371 | 9/2024 |
| WO | WO 2025/068907 | 4/2025 |
| WO | WO 2025/068922 | 4/2025 |

OTHER PUBLICATIONS

Cavana et al., "A pilot Study of the efficacy of wipes containing chlorhexidine 0.3%, climbazole 0.5% and Tris-EDTA to reduce Malassezia pachydermatis populations on canine skin", Veterinary Dermatology, Jun. 2015, vol. 26, p. 278-e61.
Finnegan et al., "EDTA: An Antimicrobial and Antibiofilm" Advances in Wound Care, Advances in Wound Care, Jun. 2015, vol. 4(7), p. 415-421.
Hill et al., "Efficacy of 4% tetrasodium ethylenediaminetetraacetic acid (T-EDTA) catheter lock solution in home parenteral nutrition patients: A quality improvement evaluation", Journal of Vascular Access, Jul. 2021, vol. 22(4), pp. 533-539.
Liu et al., "In vitro and in vivo Activity of EDTA and antibacterial agents against biofilms of mucoid Pseudomonas aeruginosa", Infection, Feb. 2017, 45(1), pp. 23-31.
Machado et al., "Inhibition of Severe Acute Respiratory Syndrome Coronavirus 2 Replication by Hypertonic Saline Solution in Lung and Kidney Epithelial Cells", ACS Pharmacology & Translational Science, 2021, vol. 4, pp. 1514-1527.
Massip-Copiz et al., "Extracellular pH and lung infections in cystic fibrosis", European Journal of Cell Biology, Aug. 2018, vol. 97(6), pp. 402-410.
Nechipurenko et al., "The role of acidosis in the pathogenesis of severe forms COVID-19", Biology, 2021, vol. 10 (852), pp. 1-15, (retrieved from: https://www.ncbi.nlm.nih.gov/pmc/articles/PMC8469745/).
Puvvadi et al., "Role of Tris-CaEDTA as an adjuvant with nebulised tobramycin in cystic fibrosis patients with Psuedomonas aeruginosa lung infections: A randomised controlled trial" Journal of Cystic Fibrosis, 2021, vol. 20, pp. 316-323.
Sivaranjani, et al., "Synergistic activity of terasodium EDTA, ethanol and chlorhexidine hydrochloride against planktonic and biofilm cells of clinicallyrelevant pathogens". Journal of Global Antimicro-

(56) References Cited

OTHER PUBLICATIONS bial Resistance, Mar. 2021 (Mar. 2021), vol. 24, pp. 148-157. [online] [retrieved on Oct. 20, 2022 (Oct. 20, 2022). Retrieved from the Internet: https://www.sciencedirect.com/science/article/pii/S2213716520303155>.
Voor in 't Holt et al., "Antiseptic Barrier Cap Effecive in Reducing Central Line-Associated Bloodstream Infections: A Systemic Review and Meta-Analysis", International Journal of Nursing Studies, Apr. 2017, vol. 69, pp. 34-40.
Wark et al., "Nebulised hypertonic saline for cystic fibrosis", Cochrane Database Systemic Reviews, 2018, Issue 9, Art No. CD001506 (retrieved from: https://wwwucbi.nlm.nih.gov/pmc/articles/PMC65135957).
PCT Application No. PCT/IB2022/056951, International Search Report and Written Opinion dated Oct. 31, 2022.
PCT Application No. PCT/IB2022/056951, International Preliminary Report on Patentability dated Feb. 8, 2024.
PCT Application No. PCT/IB2023/051636, International Search Report and Written Opinion dated Jun. 6, 2023.
PCT Application No. PCT/IB2023/051639, International Search Report and Written Opinion dated May 10, 2023.
PCT Application No. PCT/IB2023/051641, International Search Report and Written Opinion dated May 10, 2023.
PCT Application No. PCT/IB2023/053034, International Search Report and Written Opinion dated Jul. 13, 2023.
K. Ito et al., "Molecular states of fungal nuclease composed of heterogeneous subunits as estimated from the effects of urea and chelating agents," Archives of Biochemical Biophysics 317, No. 1 (Feb. 20, 1995): 25-32, doi: 10.1006/abbi.1995.1131 and https://pubmed.ncbi.nlm.nih.gov/7872791/.
Katsanos AH, Tsivgoulis G. Is intravenous thrombolysis still necessary in patients who undergo mechanical thrombectomy? Curr Opin Neurol. Feb. 2019;32(1):3-12. https://pubmed.ncbi.nlm.nih.gov/30461464/.
Mohammadi et al., Elmira; "Reteplase: Structure, Function, and Production," Adv Biomed Res. 8 (2019): 19, doi: 10.4103/abr.abr_169_18 and https://www.ncbi.nlm.nih.gov/pmc/articles/PMC6446582/.
Mosimah CI, Murray PJ, Simpkins JW. Not all clots are created equal: a review of deficient thrombolysis with tissue plasminogen activator (tPA) in patients with metabolic syndrome. Int J Neurosci. Jun. 2019;129(6):612-618. https://www.ncbi.nlm.nih.gov/pmc/articles/PMC6443479/.
Moureau et al., Nancy L.; "The Use of Alteplase for Treatment of Occluded Central Venous Catheters in Home Care," Journal of the Association for Vascular Access 10, No. 3 (Sep. 2005):123-129, DOI: 10.2309/java.10-3-7 and https://www.researchgate.net/publication/233615106_The_Use_of_Alteplase_for_Treatment_of_Occluded_Central_Venous_Catheters_in_Home_Care.
Muhammad, Baig, Bodle J. Thrombolytic Therapy. [Updated Jun. 17, 2021]. In: StatPearls [Internet]. Treasure Island (FL): StatPearls Publishing; Jan. 2021—https://www.ncbi.nlm.nih.gov/books/NBK557411/. Discusses a variety of thrombolytic agents.
Naika, Gajendra S. and Tiku, Purnima K., "Influence of ethylenediaminetetraacetic acid (EDTA) on the structural stability of endoglucanase from Aspergillus aculeatus," J. Agric. Food Chem. 59, No. 13 (Jul. 13, 2011): 7341-5, DOI: 10.1021/jf103889m and https://pubmed.ncbi.nlm.nih.gov/21651310/.
National Institutes of Health, National Library of Medicine. Thrombolytic therapy..[Downloaded: Aug. 10, 2022].
Ouellet, "POS-602 Tetrasodium Edta Reduces Alteplase Use in Patients With Dysfunctional Hemodialysis Catheters," Ki Reports, vol. 6, Issue 4, Supplement, S263, Apr. 1, 2021, DOI: https://doi.org/10.1016/j.ekir.2021.03.631.
Quirt et al., Jill; "Reduction of Central Line-Associated Bloodstream Infections and Line Occlusions in Pediatric Intestinal Failure Patients Receiving Long-Term Parenteral Nutrition Using an Alternative Locking Solution, 4% Tetrasodium Ethylenediaminetetraacetic Acid," J. Parenteral and Enteral Nutrition, 45, No. 6 (Aug. 2021): 1286-1292, doi: 10.1002/jpen.1989 and https://pubmed.ncbi.nlm.nih.gov/32770561/.
RadiologyInfo.org._Catheter-directed_Thrombolysis. [Downloaded: Aug. 31, 2022].
Reed, Mirembe; Connor C. Kerndt, and Diala Nicolas, "Alteplase," StatPearls [Internet], Last Update: Jul. 12, 2022, https://www.ncbi.nlm.nih.gov/books/NBK499977/.
Saeed AA, Abbas Q, Ishaque S, Saeed B, Ui Haque A. Thrombolysis Using Tissue Plasminogen Activator: Experience from a Critical Care Setting. Indian J Hematol Blood Transfus. Oct. 2018;34(4):723-726. https://pubmed.ncbi.nlm.nih.gov/30369748/.
Shavit et al., Linda; "Urokinase for restoration of patency of occluded permanent central venous access in haemodialysis patients—a new protocol," Nephrology Dialysis Transplantation, vol. 22, Issue 2, Feb. 2007, pp. 666-667, https://doi.org/10.1093/ndt/gfl571 and https://academic.oup.com/ndt/article/22/2/666/1886790.
Singha et al., Priyadarshini; "A Review of the Recent Advances in Antimicrobial Coatings for Urinary Catheters," Acta Biomater. 50 (Mar. 1, 2017): 20-40, doi: 10.1016/j.actbio.2016.11.070.
Society for Vascular Surgery. Thrombolytic Therapy. [Downloaded: Aug. 31, 2022].
Szymanska et al., Joanna; "Locked Away—Prophylaxis and Management of Catheter Related Thrombosis in Hemodialysis," J. Clin Med. 10, No. 11 (Jun. 2021): 2230, doi: 10.3390/jcm10112230 and https://www.ncbi.nlm.nih.gov/pmc/articles/PMC8196553/.
"Tenecteplase, TNK-tPA injection," https://my.clevelandclinic.org/health/drugs/20030-tenecteplase-tnk-tpa-injection. [Downloaded: Aug. 10, 2022].
Baig, et al., "Thrombolytic Therapy", StatPearls [Internet], Jan. 2022, StatPearls Publishing, Treasure Island, FL, https://www.ncbi.nlm.nih.gov/books/NBK557411/. Discusses a variety of thrombolytic agents.
PCT Application No. PCT/IB2023/051636, International Preliminary Report on Patentability dated Sep. 6, 2024.
PCT Application No. PCT/IB2023/051639, International Preliminary Report on Patentability dated Sep. 6, 2024.
PCT Application No. PCT/IB2023/051641, International Preliminary Report on Patentability dated Sep. 6, 2024.
PCT Application No. PCT/IB2023/053034, International Preliminary Report on Patentability dated Oct. 10, 2024.
PCT Application No. PCT/IB2024/059351, International Search Report and Written Opinion dated Jan. 6, 2025.
PCT Application No. PCT/IB2024/059371, International Search Report and Written Opinion dated Jan. 10, 2025.
Winnicki et al., "Taurolidine-based catheter lock regimen significantly reduces overall costs, infection, and dysfunction rates of tunneled hemodialysis catheters," Kidney International 93:753-760, 2018.
U.S. Appl. No. 18/112,674, Office Action dated Jun. 2, 2025.
Manrique-Rodriguez, Silvia, et al., "Standardization and Chemical Characterization of Intravenous Therapy in Adult Patients: A Step Further in Medication Safety", Drugs R D. Mar. 2021;21(1):39-64. doi: 10.1007/s40268-020-00329-w. Epub Dec. 21, 2020. Erratum in: Drugs R D Jun.;21(2):239-265 (Year: 2020).
U.S. Appl. No. 18/112,674, Final Office Action dated Nov. 4, 2025.
U.S. Appl. No. 18/112,625, Office Action dated Sep. 25, 2025.
U.S. Appl. No. 18/112,648, Office Action dated Nov. 21, 2025.
UAE Application No. P2024-02193, Office Action dated Nov. 26, 2025.
EP Application No. 23759408.0, Extended European Search Report dated Nov. 18, 2025.
24871154.1, EP, Karen Bernice Mueller, Aerosol Delivery of EDTA Compositions, filed Apr. 22, 2026.
24871157.4, EP, Karen Bernice Mueller, Topical Delivery of EDTA Compositions, filed Apr. 22, 2026.
U.S. Appl. No. 19/556,222, Karent Bernice Mueller, Products, Methods, and Systems for Implantable Medical Devices, filed Mar. 4, 2026.
PCT/IB2026/052099, WO, Karen Bernice Mueller, Products, Methods, and Systems for Implantable Medical Devices, filed Mar. 4, 2026.

(56) References Cited

OTHER PUBLICATIONS

Al-Amin AH, Sarveswaran J, Wood JM, et al. Efficacy of taurolidine on the prevention of catheter-related bloodstream infections in patients on home parenteral nutrition. J Vasc Access. 2013;14(4): 379-382.
Beath S, Pironi L, Gabe S, et al. Collaborative strategies to reduce mortality and morbidity in patients with chronic intestinal failure including those who are referred for small bowel transplantation. Transplantation. 2008;85(10):1378-1384.
Belza C, Fitzgerald K, de Silva N, et al. Predicting Intestinal adaptation in pediatric intestinal failure: a retrospective cohort study. Ann Surg. 2017.
Bhagat, Renu et al., "Growth Response of Pseudomonas stutzeri RS34 to Ethylenediaminetetraacetic (EDTA) and its Interaction with Zinc," Indian Journal of Experimental Biology, vol. 31, pp. 590-594 (Jul. 1993) (Abstract Only).
Bisseling TM, Willems MC, Versleijen MW, et al. Taurolidine lock is highly effective in preventing catheter-related bloodstream infections in patients on home parenteral nutrition: a heparin-controlled prospective trial. Clin Nutr. 2010;29(4):464-846.
Casey L, Lee K-H, Rosychuk R, et al. 10-year review of pediatric intestinal failure: clinical factors associated with outcome. Nutr Clin Pract. 2008;23(4):436-442.
Chu HP, Brind J, Tomar R, et al. Significant reduction in central venous catheter-related bloodstream infections in children on HPN after starting treatment with taurolidine line lock. J Pediatr Gastroenterol Nutr. 2012:55(4):403-407.
Colobert, Louis "Etude de la Lyse de *Salmonelles* Pathogenes Provoquee Par le Lysozyme, Apres Delipidation Partielle de la Paroi Externe," Annales de L'Institut Pasteur, 1958, pp. 156-167. (English translation Not Available).
Corrigan M, Kirby DF. Impact of a national shortage of sterile ethanol on a home parenteral nutrition practice: a case series. JPEN J Parenter Enteral Nutr. 2012;36(4):476-480.
Dannenberg C Bu, Rothe A, Beet J, Korholz D. Ethanol-lock technique in the treatment of bloodstrem infections in pediatric oncology patients with broviac catheter. J Pediatr Hematol Oncol. 2003;25(8):616-621.
Diamond IR, de Silva N, Pencharz PB, et al. Neonatal short bowel syndrome outcomes after the establishment of the first Canadian multidisciplinary intestinal rehabilitation program: preliminary experience. J Pediatr Surg. 2007;42(5):806-811.
Diamond IR, de Silva NT, Tomlinson GA, et al. The role of parenteral lipids in the development of advanced intestinal failure-associated liver disease in infants: a multiple-variable analysis. JPEN J Parenter Enteral Nutr. 2011;35(5):596-602.
Gray, G.W. et al., "Effect of Ethylenediaminetetra-acetic Acid on the Cell Walls of Some Gram-Negative Bacteria," J. Gen Microbiol., vol. 39, pp. 385-399 (1965).
Gray, G.W. and Wilkinson, S.G., "The Action of Ethylenediaminetetra-acetic Acid on Pseudomonas aeruginosa," J. appl. Bact. 28 (1), 1965, pp. 153-164.
Grula, E.A. and Hartsell S.E., "Lysozyme in the Bacteriolysis of Gram-Negative Bacteria," II. Factors Influencing Clearing During the Nakamura Treatment, Canadian Journal of Microbiology, vol. 3 , 1957, pp. 23-34.
Haque, H. et al., "Effect of Chelating Agents on the Susceptibility of Some Strains of Gram-Negative Bacteria to Some antibacterial Agents," Antimicrobial Agents and Chemotherapy., vol. 6, No. 2, pp. 200-206 (Aug. 1974).
Haque, H. et al., "Effect of Ethylenediaminetetraacetic Acid and Related Chelating Agents on whole Cells of Gram-Negative Bacteria,". Antimicrobial Agents and Chemotherapy., vol. 5, No. 5, pp. 447-452 (May 1974).
Harper, W.E.S. et al., "Effect of Chlorhexidine/EDTA/Tris Against Bacterial Isolates from Clinical Specimens," Microbios, vol. 21, pp. 107-112 (1987) (Abstract only).
Hess RA, Welch KB, Brown PI, et al. Survival outcomes of pediatric intestinal failure patients: analysis of factors contributing to improved survival over the past two decades. J Surg Res. 2011;170(1):27-31.
Hamilton-Miller, J.M.T., "Effect of EDTA Upon Bacterial Permeability to Benzylpenicillin," Biochemical and Biophysical Research Communications, vol. 20, No. 6, 1965.
Hamilton-Miller, J.M.T., "Damaging Effects of Ethylenediaminetetra-acetate and Penicillins on Permeability Barriers in Gram-negative Bacteria," Alterations to Bacterial Permeability, vol. 1966, vol. 100, pp. 675-682.
Howard L, Ashley C. Management of complications in patients receiving home parenteral nutrition. Gastroenterology. 2003;124(6):1651-1661.
Izzat, I.N., et al., "Effect of varying concentrations of EDTA on the antimicrobial properties of cutting fluid preservatives," Microbios, vol. 26, No. 103, pp. 37-44 (1979). Abstract Only.
Kanaa M, Wright MJ, Akbani H, et al. Cathasept line lock and microbial colonization of tunneled hemodialysis catheters: a multicenter randomized controlled trial. Am J Kidney Dis. 2015;66(6): 1015-1023.
Kaufman SS, Atkinson JB, Bianchi A, et al. Indications for pediatric intestinal transplantation: a position paper of the American Society of Transplantation. Pediatr Transplant. 2001;5(2):80-87.
Kite P, Eastwood K, Sugden S, et al. Use of in vivo-generated biofilms from hemodialysis catheters to test the efficacy of a novel antimicrobial catheter lock for biofilm eradication in vitro. J Clin Microbiol. 2004;42(7):3073-3076.
Kraniak, J.M. et al., "Effect of Ethylenediaminetetraacetic Acid (EDTA) and Metal Ions on Growth of *Staphylococcus aureus* 196E in Culture Media," Journal of Food Science, vol. 53, No. 3, pp. 910-913 (1988).
Lee I, Neil JJ, Huettner PC, et al. The impact of prenatal and neonatal infection on neurodevelopmental outcomes in very preterm infants.J Perinatol. 2014;34(10):741-747.
L. Leive, V. K. Shovlin, S. E. Mergenhagen "Physical, Chemical, and Immunological Properties of Lipopolysaccharide Released from *Escherichia coli* by Ethylenediaminetetraacetate," The Journal of Biological Chemistry, 1968, vol. 243, No. 24, issue of Dec. 25, pp. 6384-6391.
Liu, Fangning, et al., "Tetrasodium EDTA Is Effective at Eradicating Biofilms Formed by Clinically Relevant Microorganisms from Patients' Central Venous Catheters," mSphere, Nov./Dec. 2018, vol. 3, Issue 6 (16 pages).
Malhotra S., et al., "One vs Two Applications of Chlorhexidine/Ethanol for Disinfecting the Skin: Implications for Regional Anaesthesia", *Anaesthesia, Blackwell Science Ltd*, GB, vol. 66, No. 7, May 24, 2011, pp. 574-578.
Metcalf SC, Chambers ST, Pithie AD. Use of ethanol locks to prevent recurrent central line sepsis. J Infect. 2004;49(1):20-22.
Mouw E, Chessman K, Lesher A, et al. Use of an ethanol lock to prevent catheter-related infections in children with short bowel syndrome. J Pediatr Surg. 2008;43(6):1025-1029.
Nex Medical Antiseptics S.r.l., "Sani-Cloth CHG 2%—Information for Use (IFU)", Jul. 23, 2020, pp. 1-6, XP093343150, retrieved from the Internet: URL: https://pdihc.com/global/wp-content/uploads/sites/2/2019/07/IFU-14-Rev-1-Sani-Cloth-CHG-2.pdf [retrieved on Dec. 3, 2025].
O'Grady NP, Alexander M, Burns LA, et al. Guidelines for the prevention of intravascular catheter-related infections. Clin Infect Dis. 2011;52(9):e162-e193.
Oliveira C, Nasr A, Brindle M, et al. Ethanol locks to prevent catheter related bloodstream infections in parenteral nutrition: a meta-analysis. Pediatrics. 2012;129(2):318-329.
Onland W, Shin CE, Fustar S, et al. Ethanol-lock technique for persistent bacteremia of long-term intravascular devices in pediatric patients. Arch Pediatr Adolesc Med. 2006;160(10):1049-1053.
Percival SL, Kite P, Eastwood K, et al. Tetrasodium EDTA as a novel central venous catheter lock solution against biofilm. Infect Control Hosp Epidemiol. 2005;26(6):515-519.
Pittet D, Tarara D, Wenzel RP. Nosocomial bloodstream infection in critically ill patients. Excess length of stay, extra costs, and attributable mortality. JAMA. 1994;271(20):1598-1601.

(56) References Cited

OTHER PUBLICATIONS

Raad, Issam et al., "In Vitro and Ex Vivo Activities of Minocycline and EDTA Against Microorganisms Embedded in Biofilm on Catheter Surfaces," Antimicrobial Agents and Chemotherapy, vol. 47, No. 11, pp. 3580-3585 (Nov. 2003).
Raad I, Hanna H, Maki D. Intravascular catheter-related infections: advances in diagnosis, prevention, and management. Lancet Infect Dis. 2007;7(10):645-657.
Raad II, Luna M, Khalil SA, et al. The relationship between the thrombotic and infectious complications of central venous catheters. JAMA. 1994;271(13):1014-1016.
Raad II, Hanna HA. Intravascular catheter-related infections: new horizons and recent advances. Arch Intern Med. 2002;162(8):871-878.
Ralls MW, Blackwood RA, Arnold MA, et al. Drug shortage associated increase in catheter-related blood stream infection in children. Pediatrics. 2012;130(5):e1369-e1373.
Rello J, Ochagavia A, Sabanes E, et al. Evaluation of outcome of intravenous catheter-related infections in critically ill patients. Am J Respir Crit Care Med. 2000;162(3 Pt 1):1027-1030.
Restrepo D, Laconi NS, Alcantar NA, et al. Inhibition of heparin precipitation, bacterial growth, and fungal growth with a combined isopropanol-ethanol locking solution for vascular access devices. J Pediatr Surg. 2015;50(3):472-477.
Root, et al., "Inhibitory Effect of Disodium EDTA upon the Growth of *Staphylococcus epidermidis* In Vitro: Relation to Infection Prophylaxis of Hickman Catheters", Antimicrobial Agents and Chemotherapy. Nov. 1988, p. 1627-1631.
Said, A.A. et al., "Expression of H1 Outer-Membrane Protein of Pseudomonasaeruginosa in Relation to Sensitivity to EDTA and Polymyxin B," J. Med. Microbiol., vol. 24, pp. 267-274 (1987).
Sanders J, Pithie A, Ganly P, et al. A prospective double-blind randomized trial comparing intraluminal ethanol with heparinized saline for the prevention of catheter-associated bloodstream infection in immunosuppressed haematology patients. J Antimicrob Chemother. 2008;62(4):809-915.
Schilcher G, Schlagenhauf A, Schneditz D, et al. Ethanol causes protein \precipitation—new safety issues for catheter locking techniques. PLoS One. 2013;8(12):e84869.
Schlapbach LJ, Aebischer M, Adams M, et al. Impact of sepsis on neurodevelopmental outcome in a Swiss National Cohort of extremely premature infants. Pediatrics. 2011;128(2):e348.
Schoot RA, van Ommen CH, Stijnen T, et al. Prevention of central venous catheter-associated bloodstream infections in paediatric oncology patients using 70% ethanol locks: A randomised controlled multicentre trial. Eur J Cancer. 2015;51(14):2031-2038.
Shah DK, Doyle LW, Anderson PJ, et al. Adverse neurodevelopment in preterm infants with postnatal sepsis or necrotizing enterocolitis is mediated by white matter abnormalities on magnetic resonance imaging at term. J Pediatr. 2008;153(2):170-5, 75.el.
Shatnawei A, Parekh NR, Rhoda KM, et al. Intestinal failure management at the Cleveland Clinic. Arch Surg. 2010;145(6):521-527.
So S, Patterson C, Gold A, et al. Neurodevelopmental outcomes of infants with intestinal failure at 12 and 26 months corrected age. Early Hum Dev. 2019;130:38-43.
Sondheimer JM AE, Cadnapaphornchai M. Infection and cholestasis in neonates with intestinal resection and long-term parenteral nutrition. J Pediatr Gastroenterol Nutr. 1998;27(2):131-137. (Abstract Only).
Struijs MC, Diamond IR, de Silva N, et al. Establishing norms for intestinal length in children. J Pediatr Surg. 2009;44(5):933-938 (Abstract Only).
System NNIS. National nosocomial infections surveillance system report, data summary from Jan. 1992 through Jun. 2004. Am J Infect Control. 2004;32(8):470-485.
Wales PW, de Silva N, Kim JH, et al. Neonatal short bowel syndrome: a cohort study. J Pediatr Surg. 2005;40(5):755-762.
Wales PW, Kosar C, Carricato M, et al. Ethanol lock therapy to reduce the incidence of catheter-related bloodstream infections in home parenteral nutrition patients with intestinal failure: preliminary experience. J Pediatr Surg. 2011;46(5):951-956.
Westgate, R., et al., "Effect of Exposure to Chlorhexidine Residues at 'During Use' Concentrations on Antimicrobial Susceptibility Profile, Efflux, Conjugative Plasmid Transfer, and Metabolism of *Escherichia coli*", Antimicrobial Agents Chemotherapy, Dec. 2020, vol. 64, Issue 12.
Wolf J, Connell TG, Allison KJ, et al. Treatment and secondary prophylaxis with ethanol lock therapy for central line-associated bloodstream infection in paediatric cancer: a randomised, doubleblind, controlled trial. Lancet Infect Dis. 2018;18(8):854-863.
Wolf J, Shenep JL, Clifford V, et al. Ethanol lock therapy in pediatric hematology and oncology. Pediatr Blood Cancer. 2013;60(1):18-25.
M. J. Wolin, "Lysis of Vibrio succinogenes by Ethylenediaminetetraacetic Acid of Lysozyme," Journal of Bacteriology, May 1966, vol. 91, No. 5, pp. 1781-1786.
Sivaranjani, et al., "Synergistic activity of terasodium EDTA, ethanol and chlorhexidine hydrochloride against planktonic and biofilm cells of clinicallyrelevant pathogens". Journal of Global Antimicrobial Resistance, Mar. 2021 (Mar. 2021), vol. 24, pp. 14.
Zimlichman E, Henderson D, Tamir O, et al. Health care-associated infections: a meta-analysis of costs and financial impact on the US health care system. JAMA Intern Med. 2013;173(22):2039-2046.
PCT Application No. PCT/IB2024/059351, International Preliminary Report on Patentability dated Apr. 9, 2026.
PCT Application No. PCT/IB2024/059371, International Preliminary Report on Patentability dated Apr. 9, 2026.
U.S. Appl. No. 18/112,625, Final Office Action dated Apr. 22, 2026.
EP Application No. 23759406.4, Extended European Search Report dated Dec. 17, 2025.
UAE Application No. P2024-02191, Office Action dated Feb. 23, 2026.
EP Application No. 23759407.2, Extended European Search Report dated Feb. 5, 2026.
U.S. Appl. No. 18/112,674, Non-Final Office Action dated Feb. 24, 2026.
U.S. Appl. No. 18/112,648, Final Office Action dated Apr. 2, 2026.
U.S. Appl. No. 18/127,175, Office Action dated Apr. 16, 2026.
TW Application No. 111128029, Office Action dated Apr. 14, 2026 (with Google Translation).
SA Application No. 1120244721, First Examination Report dated Mar. 18, 2026.
TW Application No. 111128029, Office Action dated Apr. 14, 2026.
U.S. Appl. No. 18/896,145, US, Karen Bernice Mueller, Aerosol Delivery of EDTA Compositions, filed Sep. 25, 2024.
U.S. Appl. No. 18/896,413, US, Karen Bernice Mueller, Topical Delivery of EDTA Compositions, filed Sep. 25, 2024.
UAE Application No. P2024-02186, Examination Report dated May 22, 2026.

* cited by examiner

SYNERGISTIC ACTIVITY OF NOVEL COMPOUNDS AGAINST PLANKTONIC AND BIOFILM CELLS OF CLINICALLY RELEVANT PATHOGENS

CROSS-REFERENCE TO RELATED APPLICATION

This application claims benefit of U.S. Provisional Patent Application No. 63/226,109, which was filed in the U.S. Patent and Trademark Office on Jul. 27, 2021, and Taiwan Patent Application No. 111128029, which was filed in the Taiwan Patent Office on Jul. 26, 2022, the entire contents of which are incorporated herein by reference for all purposes.

BACKGROUND OF THE INVENTION

Biofilms associated with implantable medical devices and wounds are clinically relevant, often requiring a repeated usage of antibiotics without success. The number of patients predisposed to hospital-acquired infections has been on the rise owing to an increase in patients with impaired immunity and chronic diseases and the administration of immunosuppressants or anticancer agents. Patients in the intensive care unit (ICU) are more susceptible to hospital-acquired infections than those in general wards and are susceptible to infection with pathogenic micro-organisms through various implantable medical devices. In particular, central venous access devices (CVADs) are among the most common sources of healthcare-associated bloodstream infections world-wide, with a mortality rate of 12-25%. The use of long-term CVADs is inevitable for patients admitted in nephrology, oncology, and ICUs owing to the ease of administration of blood products, fluids, parenteral nutrients, and medical therapies to the blood-stream. Unfortunately, CVADs are prone to complications such as occlusion, clot formation, and microbial colonization, all of which lead to prolonged hospitalization, expensive treatments, and significant mortality and morbidity. It has been estimated that nearly 30,000 central-line-associated bloodstream infections (CLABSIs) occur annually in acute-care facilities with an economic impact of US $46,000 per case.

Microbial colonization of CVADs is a crucial risk factor in the pathogenesis of any catheter-related sepsis. The most common pathogens associated with CLABSIs are coagulase-negative staphylococci, *Staphylococcus aureus, Pseudomonas aeruginosa*, Esc/Jeric/Jia *coli*, and *Candida* spp. The ability of these pathogens to form biofilms is one of the essential mechanisms in the pathogenesis of CLABSIs, which facilitates adhesion and colonization of the luminal surface of the catheter, a fact leading to persistent and recurrent infections. Biofilms are structured multicellular communities in which microbial cells become irreversibly attached to surfaces and are embedded in a matrix of self-secreted extracellular polymeric substances (i.e., polysaccharides, proteins, and nucleic acids). Biofilms formed within CVADs are resistant to systemic antibiotic therapy alone, with 10- to 1000-fold greater resistance to conventional antibiotics than planktonic cells. Appropriate control measures and management of catheter-related infections have become a significant challenge for physicians.

To salvage long-term CVADs, the use of antimicrobial lock solutions (ALSs) has been proposed in addition to parenteral administration of antibiotics for the prevention and treatment of CLABSIs. Catheter lumens are locked with highly concentrated antibiotic solutions [up to 1000-fold higher than the minimum inhibitory concentration (MIC)], which are allowed to dwell for a specified time to eradicate biofilm formation. However, the prophylactic use of antibiotic locks increases concerns about the emergence of multidrug resistance among pathogens. On the other hand, the catheter lumen has traditionally been locked with heparin or saline; however, neither of these agents has the potential to inhibit or eradicate biofilms. Heparin has been shown to promote the colonization of *S. aureus* on catheter surfaces. Other agents have been approved to maintain catheter patency and decrease the risk of bacterial colonization and biofilm formation, but unfortunately have a long dwell time of at least 4 hours daily (e.g., 4-10 hours/day). However, long dwell times for antimicrobials are not practical in severely ill hospitalized patients who need different intravenous agents and blood products delivered through the catheter lumen.

What is needed is a novel composition that will provide antimicrobial activity on planktonic and biofilm cells of clinically relevant pathogens (e.g., on a central venous access device (CVAD).

SUMMARY OF THE CLAIMED INVENTION

Figure 1:
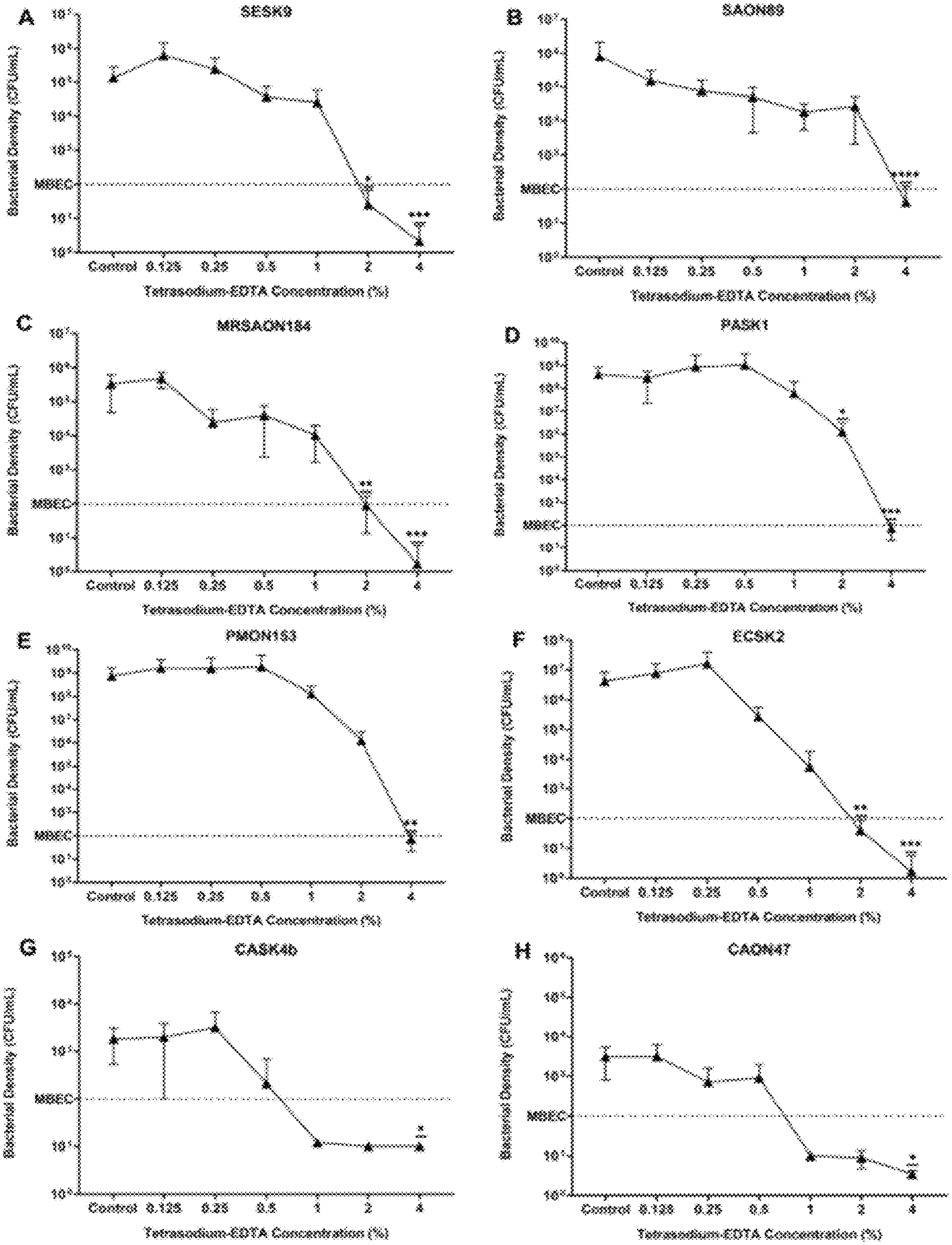
FIG. 1 is a graphical representation for the determination of the minimum biofilm eradication concentration (MBEC) for tetrasodium EDTA against Gram-positive, Gram-negative, and fungal biofilms. CFU/mL were enumerated from each peg (n-8) after biofilm growth for 48 h and following antimicrobial exposure for 24 h. Points on the graph represents the mean±standard deviation from three independent experiments. Statistical significance is indicated as follows: ‘P<0.05; “P<0.005;’ “P<0.0005;” “P<0.0001, according to an embodiment.

The present disclosure generally relates to compositions, methods of preparing, and method of use of a composition comprising: (a) about 0.05 weight % (wt %) to about 10.0 wt % of ethylenediamaminetetraacetic acid (EDTA) or other chelating agent (e.g., about 0.05 weight % (wt %) to about 10.0 wt % of tetrasodium ethylenediaminetetraacetic acid (TA); (b) from about 2.0 wt % to about 50.0 wt % of ethanol (ET), isopropyl alcohol (IPA), or a combination thereof; and (c) from about 0.015 μg/mL to about 20 mg/mL of chlorhexidine (CH) or a salt thereof (e.g., from about 0.015 μg/mL to about 0.100 μg/mL chlorhexidine or a salt thereof). The compositions, as disclosed herein, eliminate greater than 95% of planktonic or biofilm cells from a central venous access device (e.g., in a human patient).

One aspect, as disclosed herein, are compositions which demonstrate broad-spectrum antimicrobial activity on planktonic and biofilm cells of clinically relevant pathogens. The compositions comprise: (a) about 0.05 wt % to about 10.0 wt % tetrasodium ethylenediaminetetraacetic acid (TE); (b) about 2.0 wt % to about 50.0 wt % ethanol (ET); and (c) about 0.015 μg/mL to about 100.0 μg/mL chlorhexidine HCl (CH). In another aspect, the compositions comprise: (a) about 0.05 wt % to about 10.0 wt % ethylenediaminetetraacetic acid or a salt thereof; (b) about 2.0 wt % to about 50.0 wt % ethanol (ET), isopropyl alcohol (IPA), or a combination thereof; and (c) about 0.015 μg/mL to about 100.0 μg/mL chlorhexidine or a salt thereof.

The composition may be prepared by mechanical mixing, or other industry standard processing method. The composition may be prepared at any temperature suitable for mixing wherein the components do not degrade (e.g., including room temperature ±15° C.). In one aspect, the composition comprises a mixture of about 0.05 wt % to about 10.0 wt % TE; about 2.0 wt % to about 50.0 wt % ET; and about 0.015 μg/mL to about 100.0 μg/mL CH. (e.g., a 0.22 om filter). In another aspect, as disclosed herein, are methods for preparing the composition comprises: (a) contacting CH powder and water forming a mixture; (b) heating the mixture to about 30° C. to about 55° C. forming a CH solution of about 1.0 mg/mL; (c) cooling the CH solution to room temperature and passing the solution through a filter; and (d) contacting the CH solution, a solution of TE, and ET.

In yet another aspect, as disclosed herein, are methods of using the composition for eliminating planktonic or biofilm cells from a central venous access device (CVAD) in a human patient in need thereof, the method comprising contacting the CVAD with one or more of the compositions as disclosed herein. The method further comprises the utilization of a Minimum Bacterial Eradication Concentration (MBEC) value, a Minimum Inhibitory Concentration (MIC), and Minimum Fungicidal Concentration (MFC) value to determine the elimination and/or growth of planktonic or biofilm cells on a central venous access device.

Other features and iterations of the invention are described in more detail below.

DETAILED DESCRIPTION

Provided herein are compositions for eliminating planktonic or biofilm cells from a central venous access device (CVAD), methods for preparing these compositions, and methods of using the composition for eliminating planktonic or biofilm cells from a central venous access device (CVAD). Advantageously, these compositions are benign to human patients, low cost, easily prepared or manufactured, and eliminates more than 95% of the planktonic cells and eliminates more than 95% of the biofilm cells.

I. Compositions

The present disclosure encompasses compositions for eliminating planktonic or biofilm cells from a central venous access device (CVAD). These compositions may comprise (a) about 0.05 wt % to about 10.0 wt % tetrasodium ethylenediaminetetraacetic acid (TE); (b) about 2.0 wt % to about 50.0 wt % ethanol (ET); and (c) about 0.015 μg/mL to about 100.0.0 μg/mL chlorhexidine HCl (CH). These compositions are in an aqueous solution. These compositions eliminate more than 95% of the planktonic cells and eliminates more than 95% of the biofilm cells. In one embodiment, the compositions eliminate more than 95% of the planktonic cells and eliminates more than 95% of the biofilm cells from a central venous access device (CVAD) in a human patient in need thereof. In another embodiment, the compositions eliminate greater than or equal to 95%, greater than or equal to 96%, greater than or equal to 97%, greater than or equal to 98%, or greater than or equal to 99% of the planktonic cells and/or eliminates greater than or equal to 95%, greater than or equal to 96%, greater than or equal to 97%, greater than or equal to 98%, or greater than or equal to 99% of the biofilm cells from a central venous access device (CVAD) in a human patient in need thereof.

(a) ETHYLENEDIAMINETETRAACETIC ACID, A SALT THEREOF, A CHELATING AGENT, OR A COMBINATION THEREOF

The composition may comprise EDTA, a salt thereof (e.g., disodium EDTA, sodium calcium edetate, and tetrasodium EDTA), a chelating agent, or a combination thereof. EDTA or a salt thereof is an effective antimicrobial and antibiofilm agent. Generally, the composition has an EDTA or salt thereof content ranging from about 0.05 weight % (wt %) to about 10.0 wt %, about 0.05 weight % (wt %) to about 7.5 wt %, about 0.05 weight % (wt %) to about 5.0 wt %, about 0.05 weight % (wt %) to about 4.0 wt %, about 0.05 weight % (wt %) to about 3.0 wt %, about 0.5 wt % to about 5.0 wt %, about 1.0 weight % (wt %) to about 4.0 wt %, or about 0.5 weight % (wt %) to about 3.0 wt %. In other embodiments, the composition has an EDTA or salt thereof content of about 0.05 weight % (wt %) to about 1.0 wt %, about 1.0 weight % (wt %) to about 2.0 wt %, about 2.0 weight % (wt %) to about 3.0 wt %, about 3.0 weight % (wt %) to about 4.0 wt %, or about 4.0 weight % (wt %) to about 5.0 wt %. In various embodiments, the composition has an EDTA or salt thereof content of about 0.5 wt %, about 1.0 wt %, about 1.5 wt %, about 2.0 wt %, about 2.5 wt %, about 3.0 wt %, about 3.5 wt %, about 4.0 wt %, about 4.5 wt %, or about 5.0 wt %. In an embodiment, the composition has an EDTA or salt thereof content of about 3.0 wt %.

The composition may comprise chelating agents such as citric acid, nitrilotriacetic acid (NTA), ethylenediamine-N, N'-disuccinic acid (EDDS), iminodiacetic acid, 2,3-dimercaptopropanesulfonic acid (DMPS), thiamine tetrahydrofurfuryl disulfide (TTFD), dimercaptosuccinic acid, penicillamine, trientine, deferasirox, deferiprone, deferoxamine, dimercaprol, and combinations thereof. In some embodiments, the composition has a chelating agent content ranging from about 0.05 weight % (wt %) to about 10.0 wt %, about 0.5 wt % to about 5.0 wt %, about 1.0 weight % (wt %) to about 4.0 wt %, or about 0.5 weight % (wt %) to about 3.0 wt %. In other embodiments, the composition has a chelating agent content of about 0.05 weight % (wt %) to about 1.0 wt %, about 1.0 weight % (wt %) to about 2.0 wt %, about 2.0 weight % (wt %) to about 3.0 wt %, about 3.0 weight % (wt %) to about 4.0 wt %, or about 4.0 weight % (wt %) to about 5.0 wt %. In various embodiments, the composition has a chelating agent content of about 0.5 wt %, about 1.0 wt %, about 1.5 wt %, about 2.0 wt %, about 2.5 wt %, about 3.0 wt %, about 3.5 wt %, about 4.0 wt %, about 4.5 wt %, or about 5.0 wt %. In an embodiment, the composition has a chelating agent content of about 3.0 wt %.

(b) ETHANOL, ISOPROPYL ALCOHOL, OR COMBINATIONS THEREOF

The composition may comprise ethanol (ET), isopropyl alcohol (IPA), or a combination thereof. Ethanol, isopropyl alcohol, or a combination thereof can effectively kill microorganisms by dissolving their membrane lipid bilayer and denaturing their proteins. In general, the composition has an ethanol, isopropyl alcohol, or combination thereof content ranging from about 2.0 wt % to about 50.0 wt %, about 3.0 wt % to about 40.0 wt %, or about 5.0 wt % to about 30 wt %. In various embodiments, the composition has an ethanol, isopropyl alcohol, or combination thereof content of about 2.0 wt % to about 10.0 wt %, about 10.0 wt % to about 15.0 wt %, about 15.0 wt % to about 20.0 wt %, about 20.0 wt % to about 25.0 wt %, about 25.0 wt % to about 30.0 wt %, about 30.0 wt % to about 35.0 wt %, about 35.0 wt % to about 40.0 wt %, about 40.0 wt % to about 45.0 wt %, or about 45.0 wt % to about 50.0 wt %. In other embodiments, the composition has an ethanol, isopropyl alcohol, or combination thereof content of about 2.0 wt % to about 5.0 wt %, from about 5.0 wt % to about 8.0 wt %, from about 8.0 wt % to about 10.0 wt %, about 10.0 wt % to about 12.0 wt %, about 12.0 wt % to about 14.0 wt %, about 14.0 wt % to about 16.0 wt %, about 16.0 wt % to about 18.0 wt %, about 18.0 wt % to about 20.0 wt %, about 20.0 wt % to about 22.0 wt %, 22.0 wt % to about 24.0 wt %, about 24.0 wt % to about 26.0 wt %, about 26.0 wt % to about 28.0 wt %, about 28.0 wt % to about 30.0 wt %, about 30.0 wt % to about 32.0 wt %, about 32.0 wt % to about 34.0 wt %, about 34.0 wt % to about 36.0 wt %, about 36.0 wt % to about 38.0 wt %, about 38.0 wt % to about 40.0 wt %, about 40.0 wt % to about 42.0 wt %, about 42.0 wt % to about 44.0 wt %, about 44.0 wt % to about 46.0 wt %, about 46.0 wt % to about 48.0 wt %, or about 48.0 wt % to about 50.0 wt %. In various embodiments, the composition has an ethanol, isopropyl alcohol, or combination thereof content of about 2.0 wt %, about 3.0 wt %, about 4.0 wt %, about 5.0 wt %, about 6.0 wt %, about 7.0 wt %, about 8.0 wt %, about 9.0 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, or about 50 wt %. In an embodiment, the composition has an ethanol, isopropyl alcohol, or combination thereof content of about 20%.

(c) CHLORHEXIDINE, A SALT THEREOF, OR A COMBINATION THEREOF

The composition may comprise chlorhexidine, a salt thereof, or a combination thereof. The term "chlorhexidine" includes chlorhexidine HCl, as well as chlorhexidine comprising gluconic acid or acetic acid. Chlorhexidine salts included in the scope of the present invention may be chlorhexidine gluconate, chlorhexidine digluconate, chlorhexidine acetate, and combinations thereof. Chlorhexidine (1,6-bis(4-chloro-phenylbiguanido)hexane), also known as CHX or CH, is a disinfectant and antiseptic. Generally, the composition(s) of the present invention may have a chlorhexidine or a salt thereof content ranging from about 0.015 μg/mL to about 100.0 μg/mL. In various embodiments, the composition has a chlorhexidine or a salt thereof content ranging from about 0.015 μg/mL to about 100.0 μg/mL, from about 0.1 μg/mL to about 75.0 μg/mL, about 1.0 μg/mL to about 50 μg/mL, or about 2.0 μg/mL to about 10.0 μg/mL. In various embodiments, the composition has a chlorhexidine or a salt thereof content of about 0.015 μg/mL to about 1.0 μg/mL, about 1.0 μg/mL to about 5.0 g/mL, about 5.0 μg/mL to about 10.0 μg/mL, about 10.0 μg/mL to about 15.0 μg/mL, about 15.0 g/mL to about 20.0 μg/mL, about 20.0 μg/mL to about 30.0 μg/mL, about 30.0 μg/mL to about 40.0 μg/mL, about 40.0 μg/mL to about 50.0 μg/mL, about 50.0 μg/mL to about 60.0 μg/mL, about 60.0 μg/mL to about 70.0 μg/mL, about 70.0 g/mL to about 80.0 μg/mL, about 80.0 μg/mL to about 90.0 μg/mL, or about 90.0 μg/mL to about 100.0 μg/mL. In another embodiment, the composition has a chlorhexidine or a salt thereof of about 1.5 μg/mL, 2.5 g/mL, about 5.0 μg/mL, about 7.5 μg/mL. In another embodiment, the composition has a chlorhexidine or a salt thereof of about 0.015 μg/mL to about 100 μg/mL, about 100.0 μg/mL to about 200.0 μg/mL, about 200.0 g/mL to about 400.0 μg/mL, about 400.0 μg/mL to about 600.0 μg/mL, about 600.0 μg/mL to about 800.0 μg/mL, or about 800.0 μg/mL to about 1000.0 g/mL. In another embodiment, the composition has a chlorhexidine or a salt thereof of about 0.015 μg/mL to about 20.0 mg/mL, about 1.0 mg/mL to about 5.0 mg/mL, about 5.0 mg/mL to about 10.0 mg/mL, about 10.0 mg/mL to about 15.0 mg/mL, about 15.0 μg/mL to about 20.0 μg/mL. In another embodiment, the composition has a chlorhexidine or a salt thereof content ranging from about 0.015 μg/mL up to 2.00% by weight of the composition.

(d) WATER

The composition is an aqueous solution. The water used in the composition may comprise distilled, double-distilled, deionized water, purified water, or water for injection.

(e) EXEMPLARY EMBODIMENTS

In one embodiment, the composition comprises about 3.0 wt % TE, about 20 wt % ET, and about 2.5 μg/mL CH. In another embodiment, the composition comprises about 2.5 to about 5.0 wt % TE, about 17.5% to about 22.5 wt % ET, and about 1.0 to about 4.0 μg/mL CH.

(f) PROPERTIES OF THE COMPOSITION

The composition of the combination of tetrasodium EDTA, ethanol, and chlorhexidine HCl demonstrate a broad-spectrum antimicrobial activity on a variety of planktonic and biofilm cells of clinically relevant pathogens and of sessile cells. These biofilm cells comprise bacterial or fungal cells. These biofilm cells also comprise Gram-positive cells, Gram-negative cells, or a combination thereof. Additionally, these compositions provide equivalent MBEC values of single test antimicrobials at substantially lower concentrations of antimicrobials. These compositions may also eliminate a 48 hour old biofilm after a 2-hour exposure and provides a substantial reduction in biofilm cells within a 2-hour contact time. Further, these compositions may also eliminate a 48 hour old biofilm after a 1-hour exposure and provides a substantial reduction in biofilm cells within a 1-hour contact time. Further these compositions may also eliminate a 48 hour old biofilm after a 30-minute exposure and provides a substantial reduction in biofilm cells within a 30-minute contact time.

In general, the composition eliminates greater than or equal to 75% of the strains of planktonic cells. In various embodiments, the composition eliminates greater than or equal to 75%, greater than or equal to 80%, greater than or equal top 85%, greater than or equal to 90%, greater than or equal to 95%, or greater than or equal to 99% of the strains of planktonic cells.

Generally, the composition eliminates greater than or equal to 75% of the strains of biofilm cells. In various embodiments, the composition eliminates greater than or equal to 75%, greater than or equal to 80%, greater than or equal top 85%, greater than or equal to 90%, greater than or equal to 95%, or greater than or equal to 99% of the strains of biofilm cells.

In general, the composition eliminates more than 95% of the planktonic cells. In various embodiments, the composition eliminates more than 95%, more than 96%, more than 97%, more than 98%, or more than 99% of the planktonic cells.

Generally, the composition eliminates more than 95% of the biofilm cells. In various embodiments, the composition eliminated more than 95%, more than 96%, more than 97%, more than 98%, or more than 99% of the biofilm cells.

In general, the composition eliminates more than 95% of the sessile cells. In various embodiments, the composition eliminates more than 95%, more than 96%, more than 97%, more than 98%, or more than 99% of the sessile cells.

The compositions, as detailed above, eliminate greater than or equal to 99% biofilms following 24 hours of treatment or exposure.

The compositions are generally benign and effective at the concentrations as disclosed herein. The compositions described herein may be suitable for human intravenous use. The compositions described herein may also be suitable for human parenteral administration. The compositions described herein may be substantially more effective at killing planktonic cells or biofilm cells as compared to heparin or saline.

II. Methods of Preparing the Compositions

The present disclosure also encompasses methods for preparing the composition for eliminating planktonic or biofilm cells from a central venous access device (CVAD). The method comprises: (a) contacting CH powder and water forming a mixture; (b) heating the mixture to about 45° C. to about 55° C. forming a CH solution of about 1.0 mg/mL; (c) cooling the CH solution to room temperature and passing the solution through a filter; and (d) contacting the CH solution, a solution of TE, and ET forming the composition comprising: about 0.05 wt % to about 10.0 wt % TE; about 2.0 wt % to about 50.0 wt % ET; and about 0.015 μg/mL to about 100.0 μg/mL CH.

The methods may be conducted in a batch, semi-continuous, or continuous fashion. The methods may also be conducted under an inert atmosphere such as nitrogen, helium, argon, or a combination thereof.

(a) Contacting CH Powder and Water Forming a Mixture

The method commences by contacting CH powder and water forming a mixture. Generally, the CH powder and water used in the mixture may be added in any sequential order, in portions, or all at same time.

The water used in the method may be distilled, doubly distilled, deionized water, purified water or water for injection.

Various forms of mixing may be utilized in the method. Non-limiting examples of mixing may be magnetic mixing or mechanical mixing.

(b) Heating the Mixture to about 45° C. To about 55° C. Forming a CH Solution of about 1.0 mg/mL The next step in the method comprises heating the mixture to about 45° C. to about 55° C. forming a CH solution of about 1.0 mg/mL. This step utilizes the appropriate mixer as used in step (a) to ensure a solution is prepared.

The temperature of heating the CH powder and water from step (a) may range from about 45° C. to about 55° C. In various embodiments, the temperature of heating the CH powder and water may range from about 45° C. to 55° C., from 45° C. to about 48° C., from about 48° C. to about 50° C., from about 50° C. to about 53° C., or from about 53° C. to about 55° C.

In general, the duration of heating the mixture from step (b) may range from about 30 seconds to about 30 minutes until a homogeneous solution is seen visually. In various embodiments, the duration of heating the mixture from step (a) may range from about 30 seconds to about 30, from about 1 minute to about 15 minutes, or from about 15 minutes to about 30 minutes.

(c) Cooling the Solution to Room Temperature and Passing the Solution Through a Micron Filter or Bag Filter The next step in the method comprises cooling the solution to room temperature and passing the solution through a micron filter or bag filter. The micron filter may be 0.22 μm filter, a 0.20 μm filter, or a 0.10 μm filter. The bag filter may be a 0.22 μm filter, a 0.20 μm filter, or a 0.10 μm filter. One or more micron filters and/or bag filters may be used in step (c). In one embodiment, the micron filter may be a 0.22 μm filter.

This method step removes undissolved material by passing the room temperature solution through a micron filter. The filter may be an inline micron filer, a sparkler, or a standalone filter apparatus.

(d) Contacting the CH Solution, a Solution of TE, and ET Forming the Composition Comprising: About 0.05 wt % to about 10.0 wt % TE; about 2.0 wt % to about 50.0 wt % ET; and about 0.015 μg/mL to about 100.0 μg/mL CH.

The last step in the method comprises (d) contacting the CH solution, a solution of TE, and ET forming the composition comprising: about 0.05 wt % to about 10.0 wt % TE; about 2.0 wt % to about 50.0 wt % ET; and about 0.015 μg/mL to about 100.0 μg/mL CH. In general, the components of the composition may be added in any sequential order, in portions, or all at same time.

Various forms of mixing may be utilized in the method. Non-limiting examples of mixing may be magnetic mixing or mechanical mixing.

The temperature of contacting the components of the composition in step (d) may range from about 10° C. to about 40° C. In various embodiments, the temperature contacting the components of the composition in step (d) may range from about 10° C. to 50° C., from 15° C. to about 35° C., from about 20° C. to about 30° C. In one embodiment, the temperature of contacting the components of the composition in step (d) may be about 23° C. (room temperature).

III. Method of Eliminating Planktonic or Biofilm Cells from a Central Venous Access Device In still another aspect encompasses eliminating or preventing growth of the planktonic or biofilm cells from a central venous access device (CVAD). The methods comprise contacting the central venous access device (CVAD) with the compositions comprising a combination of TE, ET, and CH as described above. The method further comprises the utilization of a Minimum Bacterial Eradication Concentration (MBEC) value, a Minimum Inhibitory Concentration (MIC), and Minimum Fungicidal Concentration (MFC) value to determine the elimination and/or growth of planktonic or biofilm cells on a central venous access device.

(a) Compositions Comprising a Combination of TE, ET, and CH

The composition comprising a combination of TE, ET, and CH are described in more detail above in Section I.

(b) Applying the Compositions of a Combination of TE, ET, and CH

The compositions comprising a combination of TE, ET, and CH may be applied in various ways. Non-limiting methods of applying the composition to a central venous access device (CVAD) may be painting, soaking, rinsing, and/or spraying. Other applications include use as antimicrobial lock solution, skin disinfectant solution and wound healing applications.

(c) Duration

After the composition is applied to the central venous access device (CVAD), the composition and the central venous access device interact for a period of time to determination of the elimination and growth of the planktonic or biofilm cells. For the compositions of the current invention, the period of time necessary to eliminate the planktonic or biofilm cells (e.g., the dwell time) may be from about 30 minutes to about 1 hour, about 30 minutes to about 2 hours, or about 2 hours to about 3 hours. For the compositions of the current invention, the period of time necessary to eliminate the planktonic or biofilm cells (e.g., the dwell time) may be less than 30 minutes, less than 1 hour, less than 1.5 hours, less than 2 hours, less than 2.5 hours, less than 3 hours, or less than 3.5 hours. The CVAD may then be rinsed with distilled water or saline then reused.

(d) Determination of the Elimination and/or Growth of the Planktonic or Biofilm Cells In order to determination of the elimination and/or growth of the planktonic or biofilm cells, assays to determine the value for the Minimum Bacterial Eradication Concentration (MBEC), the Minimum Inhibitory Concentration (MIC), and Minimum Fungicidal Concentration (MFC) were conducted on each and/or mixtures of planktonic or biofilm cells (pathogens) that have been shown to effect CVADs.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The word "about": is intended to include ±5% of the value, ±10% of the value, and ±15% of the value.

As various changes could be made in the above-described methods without departing from the scope of the invention, it is intended that all matter contained in the above description and in the examples given below, shall be interpreted as illustrative and not in a limiting sense.

Materials

The following materials were sourced in the Examples noted below: Tetrasodium EDTA (KiteLock™) was sourced from SterileCare Inc. as a 40 mg/mL solution (4% solution) having a pH ~11.0 in distilled water. Chlorhexidine HCl (greater than 98%) and ethanol (>89.5 v/v) were sourced from Sigma-Aldrich and used without further purification. Mueller Hinton Broth and Mueller Hinton Broth 2 were sourced from Sigma Aldrich and used directly.

Solution and Composition Preparation

A chlorhexidine HCl solution (1 mg/mL) was prepared by dissolving the appropriate amount of chlorhexidine HCl powder in distilled water heated to 50° C., allowing the solution to cool and passing it through a 0.22 μm filter.

The composition comprising a combination of tetrasodium EDTA (4% EDTA in water), chlorhexidine HCl (1 mg/mL), and ethanol was prepared by contacting the 1 mg/mL solution of chlorhexidine HCl solution, a 4% tetrasodium EDTA solution and ethanol to the specific concentration ranges, noted below were added and mixed for 15 minutes at room temperature.

Example 1: Minimum Inhibitory Concentration (MIC) and Minimum Bactericidal Concentration (MBC) or Minimum Fungicidal Concentration (MFC) Determination The MIC was determined by the micro broth dilution method in 96-well plates. Serial two-fold dilutions of tetrasodium EDTA (from 2% to 0.015%), ethanol (from 50% to 0.1%) and chlorhexidine HCl (from 100 μg/mL to 0.025 μg/mL) were prepared in Mueller Hinton broth (MH broth) with a final volume of 90 μL per well. A 10 μL containing $1\times10^5$ bacterial cells or $2\times10^3$ fungal cells were added to each well. The inoculated plates were covered with a lid, sealed with Parafilm, and incubated for 24 h at 37° C. with slight rocking on a tilting platform shaker. After incubation, the optical density at 600 nm (OD 600) of the cultures in each well was measured using an xMark™ Microplate Absorbance Spectrophotometer (Bio-Rad). The MIC was defined as the lowest concentration of antimicrobial compound at which the culture $OD_{600}$ values was similar to uninoculated control wells. MBCs and MFCs were determined by transferring 100 μL from each well with no apparent growth onto appropriate agar plates, followed by incubation for 24 h at 37° C. See FIG. 1, FIG. 2, and FIG. 3.

Example 2: Interaction of Tetrasodium EDTA with Either Ethanol or Chlorhexidine HCl The interaction between interaction of tetrasodium EDTA with ethanol or chlorhexidine HCl was created by using checkerboard titration method using micro broth dilution in 96-well microtiter plates. The concentrations of antimicrobials used were based on previously determined MIC values. Briefly, 200 μL of two-fold dilutions of tetrasodium EDTA and ethanol or chlorhexidine HCl were prepared in MH or MH II broth with standardized cell suspension. The plate contained decreasing concentrations of tetrasodium EDTA (2%-0.015%) in columns 1-10 and decreasing concentrations of ethanol (50%-0.4%) or chlorhexidine HCl (50 μg/mL-0.0125 μg/mL) in rows A-H. Then, 10 μL of standardized cell suspension was added to each well. Microtiter plates were incubated at 37° C. for 24 h, and the results were analyzed. Each test was performed in duplicate and included a growth control without the addition of any antimicrobials.

Example 3: Biofilm Cultivation Cell Composition

The evaluation of the biofilm cultivation cell composition was evaluated using an MBEC Assay® biofilm inoculator, consisting of a polystyrene lid with 96 downward-protruding pegs and a corresponding base used to grow biofilms. A standardized inoculum was diluted in an appropriate biofilm growth medium to achieve a viable cell count of 1.5×106 CFU/mL of bacterial cells or 5×105 CFU/mL of fungal cells. Then, 150 μL of this inoculum was transferred into each appropriate well, and the peg lids were inserted into the microtiter plates. The plates were sealed with Parafilm and were incubated at optimum temperature for 48 h with slight rocking for bacteria and shaking at 200 rpm for fungal strains. After incubation, the peg lid was removed from the base and rinsed twice with sterile phosphate-buffered saline (PBS) for 2 min to remove loosely attached non-sessile cells. Before the antimicrobial challenge, the pegs in column 1 (n=8) were considered as the biofilm growth control; these pegs were removed from the lids, placed into 200 μL of recovery medium, and analyzed for starting biofilm cell numbers as described below. The rinsed pegs were placed into new 96-well plates containing two-fold dilutions of antimicrobials such as tetrasodium EDTA (4%-0.0125%), ethanol (100%-0.2%), and chlorhexidine HCl (100 μg/mL-0.4 μg/mL) in 200 μL of suitable biofilm growth medium per well and incubated at optimum temperature for 24 h. After the antimicrobial challenge, the pegs were rinsed twice with sterile PBS for 2 min and placed into a new 96-well plate containing 200 μL of recovery medium. The recovery plates were sealed with Parafilm, and biofilm cells were dislodged from the pegs by sonication for 30 min with a Branson 3510 bath sonicator. The biofilm cells in the recovery medium were serially diluted, and a drop dilution assay was performed to enumerate the viable cells. MBEC values were determined as the minimum concentration of antimicrobials that yielded a viable cell count at or lower than the 125 CFU/mL detection limit.

Example 4: Determination of Fractional Biofilm Eradication Concentration (FBEC) Index This example comprises the steps of (1) identify synergistic antimicrobial effects of tetrasodium EDTA with either ethanol or chlorhexidine HCl on established biofilms, (2) using the 'checkerboard dilution method' where (3) pegs containing biofilms were treated with a combination of tetrasodium EDTA and ethanol or with tetrasodium EDTA and chlorhexidine HCl in 200 μL of two-fold dilutions inappropriate biofilm growth medium. This is followed by step (4) that comprises eight dilution steps of tetrasodium EDTA (4%-0.015%) either with ethanol (50%-0.4%) or chlorhexidine HCl (50 μg/mL-0.4 μg/mL) and where eight growth controls are analyzed for synergistic biofilm eradication. In step (4), microtiter plates are incubated at 37° C. for 24 h. then (6), after incubation, the bacterial and fungal cells were dislodged from the pegs into the recovery medium described above.

Three 10-μL aliquots, for a total of 30 μL from each well of recovery medium, were spotted on MH agar plates and incubated for 24 hours at 37° C. The FBEC is the minimum concentration of antimicrobials in combination that completely inhibited bacterial or fungal growth on agar plates. The FBEC determination is a modification of the FICI.

Example 5: Determination of Rapid Biofilm Eradication by Tetrasodium EDTA, Ethanol, and Chlorhexidine HCl Alone or in Combination This example comprises performing biofilm growth as described above. After biofilm formation, control pegs (n=6) were removed and analyzed to determine the starting biofilm cell numbers via the drop dilution method. The 48-h old biofilms on the pegs were exposed to different concentrations of test antimicrobials, dissolved in an appropriate growth medium, for 2 hours to evaluate their efficacy alone and in combination. Antimicrobial solutions tested against each organism included each agent alone at the MBEC, double combinations at the FBEC, and triple combinations ranging from 5 to 20% ethanol, 2.5-5 μg/mL chlorhexidine HCl and 1-3% tetrasodium EDTA. Following treatment, pegs were washed twice with sterile PBS, and the biofilm cells were dislodged into recovery medium and enumerated as described above.

Example 6: Evaluation of Compositions of TE and ET, and TE and CH

Antimicrobial activity was evaluated for tetrasodium EDTA alone and in combination with either ethanol or chlorhexidine HCl against planktonic cells. All three antimicrobials significantly inhibited the growth of all test organisms with MICs ranging from 0.063% to 2% for tetrasodium EDTA, 3.125%-12.5% for ethanol, and 0.1 μg/mL-50 μg/mL for chlorhexidine HCl (Table 1). Synergy (FICI: 0.5) was detected with the combination of tetrasodium EDTA with ethanol for all test Gram-positive and fungal strains, whereas partial synergy (0.5<FICI<1.0) was observed for all Gram-negative strains. The combination of tetrasodium EDTA with chlorhexidine HCl showed indifferent activity (1<FICI: 4) against 4 of 12 test strains and synergistic or partially synergistic activity against the eight remaining strains (Table 1).

TABLE 1

Determination of the minimum inhibitory concentration (MIC) and fractional inhibitory concentration index (FICI) of tetrasodium EDTA (TE) alone and in combination with ethanol (ET) or chlorhexidine HCl (CH) against planktonic cells of bacterial and fungal organisms.

| | MIC alone | | | TE + ET in combination | | | TE + CH in combination | | |
|---|---|---|---|---|---|---|---|---|---|
| Organism | TE (%) | ET (%) | CH (μg/mL) | TE (%) | ET (%) | FICI[a] | TE (%) | CH (μg/mL) | FICI[a] |
| *Staphylococcus epidermidis* ON170 | 0.063 | 3.125 | 0.1 | 0.015 | 0.4 | 0.36 (S) | 0.063 | 0.05 | 1.5 (I) |
| *S. epidermidis* SK9 | 0.063 | 6.25 | 0.1 | 0.015 | 0.4 | 0.3 (S) | 0.015 | 0.025 | 0.5 (S) |
| *Staphylococcus aureus* ON89 | 0.063 | 6.25 | 0.1 | 0.015 | 0.4 | 0.3 (S) | 0.008 | 0.1 | 1.126 (I) |
| MRSA ON184 | 0.063 | 6.25 | 0.2 | 0.015 | 0.4 | 0.3 (S) | 0.008 | 0.2 | 1.126 (I) |
| *Stenotrophomonas maltophilia* ON17 | 0.063 | 6.25 | 0.8 | 0.031 | 0.4 | 0.72 (PS) | 0.015 | 0.2 | 0.5 (S) |
| *Pseudomonas aeruginosa* SK1 | 0.25 | 3.125 | 1.6 | 0.031 | 3.125 | 0.56 (PS) | 0.5 | 0.8 | 2.5 (I) |
| *Serratia marcescens* SK2 | 1 | 6.25 | 12.5 | 0.5 | 3.125 | 0.75 (PS) | 0.063 | 1.5 | 0.16 (S) |
| *Proteus mirabilis* ON153 | 1 | 6.25 | 50 | 0.5 | 1.6 | 0.75 (PS) | 0.063 | 0.8 | 0.08 (S) |
| *Escherichia coli* ON29 | 0.5 | 12.5 | 0.4 | 0.25 | 3.125 | 0.75 (PS) | 0.008 | 0.2 | 0.516 (PS) |
| *E. coli* SK2 | 0.5 | 12.5 | 0.4 | 0.015 | 6.25 | 0.53 (PS) | 0.008 | 0.1 | 0.266 (S) |
| *Candida albicans* SK4b | 1 | 6.25 | 1.6 | 0.25 | 1.6 | 0.5 (S) | 0.063 | 0.8 | 0.596 (PS) |
| *C. albicans* ON47 | 1 | 6.25 | 1.6 | 0.25 | 0.4 | 0.314 (S) | 0.125 | 0.8 | 0.658 (PS) |

MRSA, methicillin-resistant *S. aureus*.

Example 7: Evaluation of Composition Comprising TE, ET, and CH

The three antimicrobial agents (TE, ET, and CH) displayed broad-spectrum microbicidal activity against the 12 test organisms (See Table 2). MBC or MFC values of all test antimicrobials were either equal to or higher than their respective MICs. The combination of tetrasodium EDTA with either ethanol or chlorhexidine HCl showed synergistic and partially synergistic activity against all the test strains except *S. epidermidis* ON170, which showed additive activity with an FMCI of 1.0 (Table 2). The nature of interaction found in FICI was not always the same as the FMCI. However, none of the tested tetrasodium EDTA, ethanol, or chlorhexidine HCl combinations showed antagonism concerning the FICI and FMCI values.

TABLE 2

Determination of minimum bactericidal concentration (MBC) or minimum fungicidal concentration (MFC) and the fractional microbicidal concentration index (FMCI) of tetrasodium EDTA (TE) alone and in combination with ethanol (ET) or chlorhexidine HCl (CH) against planktonic cells of bacterial and fungal organisms.

| | MBC/MFC alone | | | TE + ET in combination | | | TE + CH in combination | | |
|---|---|---|---|---|---|---|---|---|---|
| Organism | TE (%) | ET (%) | CH (μg/mL) | TE (%) | ET (%) | FMCI[a] | TE (%) | CH (μg/mL) | FMCI[a] |
| *Staphylococcus epidermidis* ON170 | 0.5 | 6.25 | 0.8 | 0.031 | 1.6 | 0.318 (S) | 0.25 | 0.4 | 1 (A) |
| *S. epidermidis* SK9 | 0.5 | 12.5 | 0.8 | 0.031 | 3.125 | 0.312 (S) | 0.008 | 0.4 | 0.516 (PS) |
| *Staphylococcus aureus* ON89 | 1 | 25 | 0.8 | 0.25 | 3.125 | 0.375 (S) | 0.008 | 0.2 | 0.375 (S) |
| MRSA ON184 | 2 | 25 | 1.6 | 0.031 | 3.125 | 0.14 (S) | 0.125 | 0.4 | 0.312 (S) |
| *Stenotrophomonas maltophilia* ON17 | 1 | 6.25 | 3.125 | 0.125 | 1.6 | 0.381 (S) | 0.031 | 0.4 | 0.16 (S) |
| *Pseudomonas aeruginosa* SK1 | 1 | 12.5 | 3.125 | 0.031 | 6.25 | 0.531 (PS) | 0.031 | 1.6 | 0.543 (PS) |
| *Serratia marcescens* SK2 | 2 | 12.5 | 25 | 0.25 | 6.25 | 0.625 (PS) | 0.125 | 1.6 | 0.126 (S) |
| *Proteus mirabilis* ON153 | 2 | 12.5 | 50 | 0.063 | 6.25 | 0.53 (PS) | 0.125 | 1.6 | 0.09 (S) |
| *Escherichia coli* ON29 | 1 | 25 | 0.8 | 0.25 | 6.25 | 0.5 (S) | 0.008 | 0.2 | 0.258 (S) |
| *E. coli* SK2 | 0.5 | 25 | 0.8 | 0.25 | 6.25 | 0.75 (PS) | 0.015 | 0.2 | 0.23 (S) |
| *Candida albicans* SK4b | 1 | 6.25 | 3.125 | 0.25 | 3.125 | 0.75 (PS) | 0.125 | 0.8 | 0.381 (S) |
| *C. albicans* ON47 | 2 | 6.25 | 3.125 | 0.25 | 3.125 | 0.625 (PS) | 0.031 | 1.6 | 0.51 (PS) |

MRSA, methicillin-resistant *S. aureus*.

Example 8: Tetrasodium EDTA Alone or in Combination with Either Ethanol or Chlorhexidine HCl Against 48 Hour Old and Preformed Biofilms This example demonstrates using a single antimicrobial agent, effective at eradicating preformed biofilms of test pathogens, with concentrations between 4% to 0.0125% of tetrasodium EDTA, 100%-0.2% of ethanol, and 100 g/mL-0.8 g/mL of chlorhexidine HCl. As per CLSI guidelines, the MBEC is defined as the minimum concentration of an antimicrobial that eradicates 99.9% of micro-organisms (i.e., 3-log reduction) in a biofilm state compared with their respective growth controls in similar conditions. All antimicrobials achieved >99.99% (i.e., 4-log reduction) killing of bacterial biofilm cells, whereas the starting biofilm cell numbers for *C. albicans* were not enough to achieve a clinically recommended standard of biofilm killing.

Figure 2:
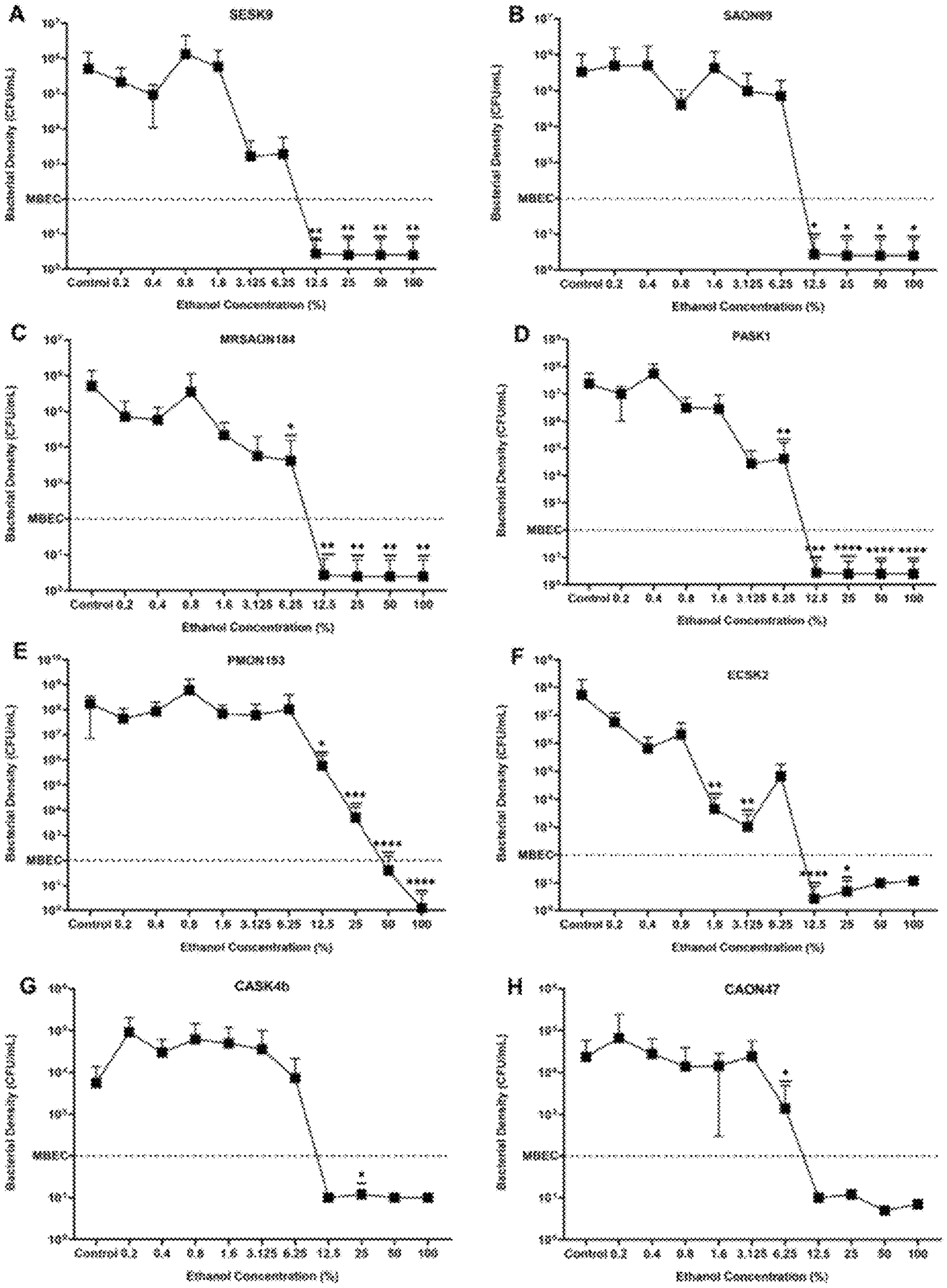
FIG. 2 is a graphical representation for a determination of the minimum biofilm eradication concentration (MBEC) for ethanol against Gram-positive, Gram-negative, and colony forming unit per milliliter of the fungal biofilms (CFU/ml) were enumerated from each peg (n-8) after biofilm growth for 48 hours and following antimicrobial exposure for 24 hours. Points on the graph represent the mean±standard deviation from three independent experiments. Statistical significance is indicated as follows: *p<0.05; P<0.005; *P<0.0005; ****p<0.0001, according to an embodiment.
Figure 3:
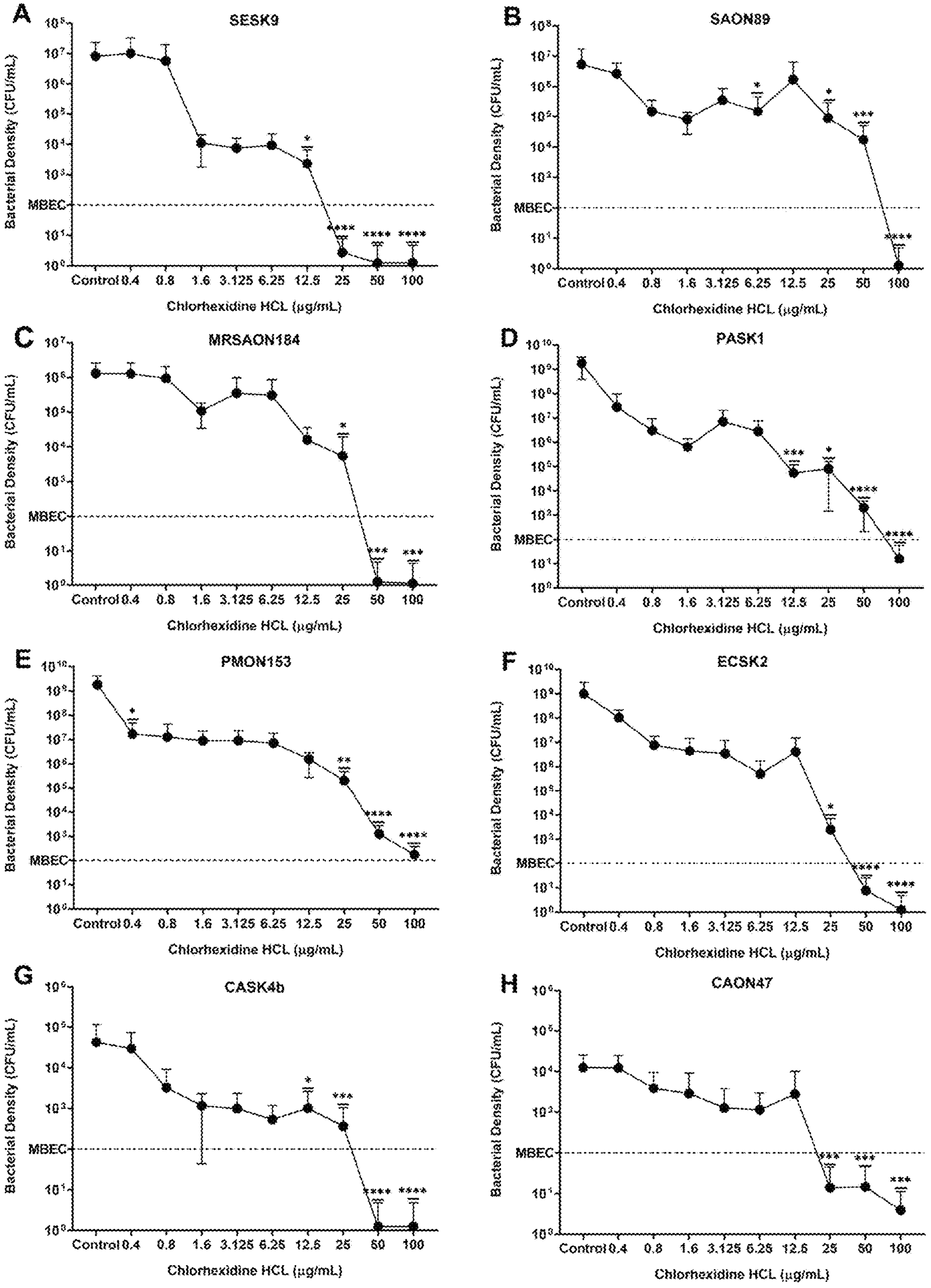
FIG. 3: is a graphical representation for a determination of the minimum biofilm eradication concentration (MBEC) for chlorhexidine HCl against Gram-positive, Gram-negative, and fungal biofilms. CFU/mL were enumerated from each peg (n-8) after biofilm growth for 48 hours and following antimicrobial exposure for 24 hours. Points on the graph represent the mean±standard deviation from three independent experiments. Statistical significance is indicated as follows: • p<0.05: “P<0.005:’ “P<0.0005:” “P<0.0001, according to an embodiment.

The MBEC of each antimicrobial agent against each test strain was established, and the data were plotted as the log reduction in the number of CFU (FIGS. 1-3). When tetrasodium EDTA was combined with either ethanol or chlorhexidine HCl, they exhibited a synergistic effect against all test strains in the study (Table 3). According to the FBEC index, the concentration of tetrasodium EDTA in combination was decreased from 1/8- to 1/64-fold (with ethanol) and 1/16- to 1/64-fold (with chlorhexidine) in comparison with its original MBEC values. Also, the required concentrations dropped by 1/4- to 1/16-fold for ethanol and 1/8- to 1/32-fold for chlorhexidine HCl when combined with tetrasodium EDTA (Table 3).

TABLE 3

Determination of the minimum biofilm eradication concentration (MBEC) and fractional biofilm eradication concentration index (FBECI) of tetrasodium EDTA (TE) alone and in combination with ethanol (ET) or chlorhexidine HCl (CH) against planktonic cells of bacterial and fungal organisms.

| | MBEC alone | | | TE + ET in combination | | | TE + CH in combination | | |
|---|---|---|---|---|---|---|---|---|---|
| Organism | TE (%) | ET (%) | CH (μg/mL) | TE (%) | ET (%) | FBECI[a] | TE (%) | CH (μg/mL) | FBECI[a] |
| *Staphylococcus epidermidis* SK9 | 2 | 12.5 | 25 | 0.031 | 1.6 | 0.14 (S) | 0.125 | 3.125 | 0.19 (S) |
| *Staphylococcus aureus* ON89 | 4 | 12.5 | 100 | 0.063 | 0.8 | 0.08 (S) | 0.125 | 3.125 | 0.06 (S) |
| MRSA ON184 | 2 | 12.5 | 50 | 0.063 | 1.6 | 0.16 (S) | 0.031 | 6.25 | 0.14 (S) |
| *Pseudomonas aeruginosa* SK1 | 4 | 12.5 | 100 | 0.125 | 3.125 | 0.28 (S) | 0.25 | 3.125 | 0.093 (S) |
| *Proteus mirabilis* ON153 | 4 | 50 | 100 | 0.125 | 6.25 | 0.16 (S) | 0.125 | 3.125 | 0.06 (S) |
| *Escherichia coli* SK2 | 2 | 12.5 | 50 | 0.125 | 1.6 | 0.19 (S) | 0.031 | 3.125 | 0.08 (S) |
| *Candida albicans* SK4b | 1 | 12.5 | 50 | 0.125 | 1.6 | 0.253 (S) | 0.063 | 6.25 | 0.18 (S) |
| *C. albicans* ON47 | 1 | 12.5 | 25 | 0.125 | 1.6 | 0.253 (S) | 0.031 | 6.25 | 0.25 (S) |

MRSA, methicillin-resistant *S. aureus*.

Figure 4:
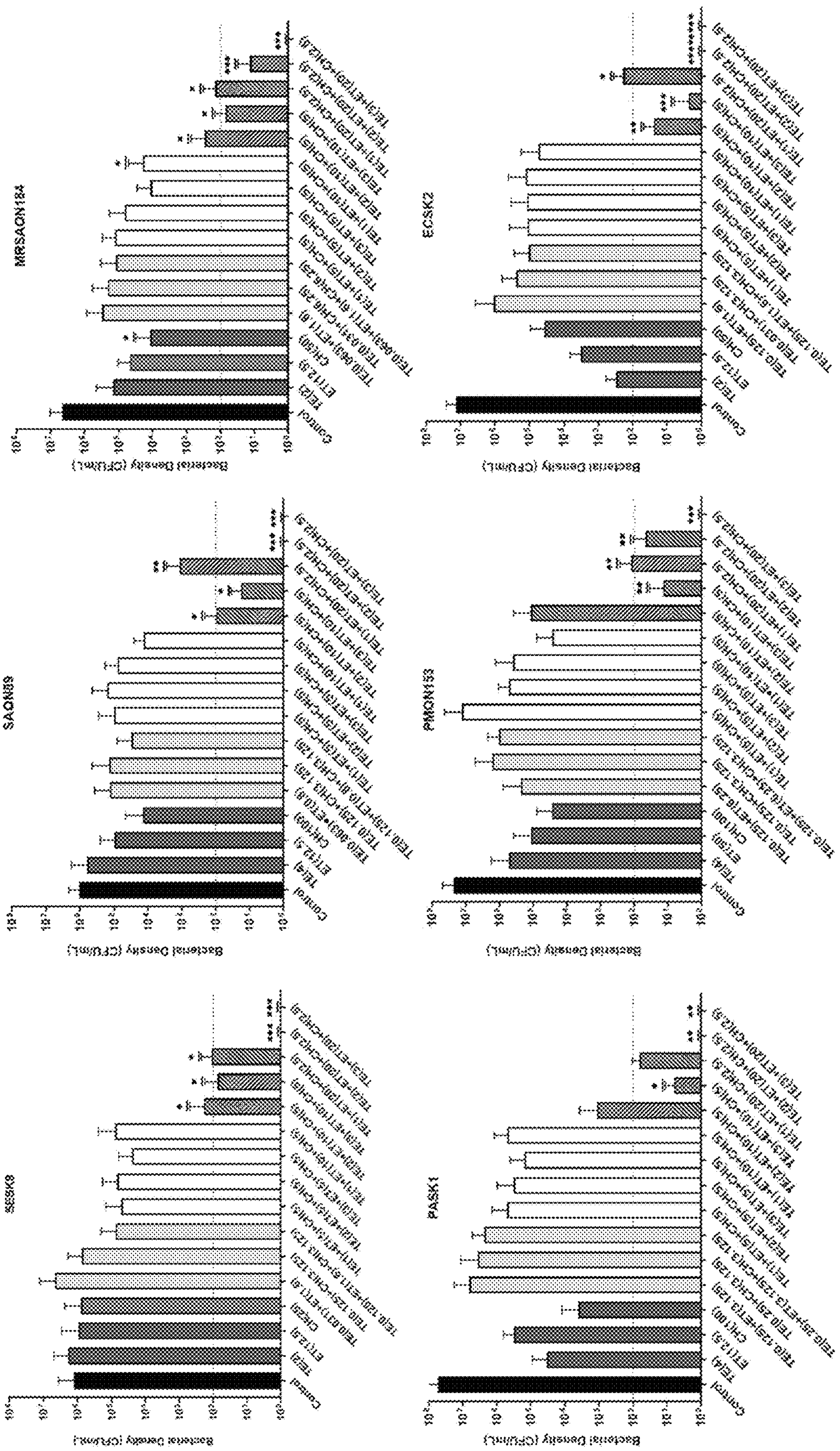
FIG. 4: is a graphical representation for the efficacy of tetrasodium EDTA (TE), ethanol (ET), and chlorhexidine HCl (CH) against Gram-positive and Gram-negative bacterial biofilms in a 2-hour exposure period. Each column represents different concentrations of test antimicrobials against each organism tested: (i) three dark grey columns represent treatment with the MBEC of TE (%), ET (%) and CH (μg/mL); (ii) three light grey column s represents treatment with the fractional biofilm eradication concentration (FBEC) of TE+ET, TE+CH, and TE+ET+CH; and (iii) white and hatched columns represent treatment with triple combinations of TE+ET+CH, with hatched bar combinations showing the best killing effects. Statistical significance was determined by comparison with non-treated biofilms (black bar) and is indicated as follows: •p<0.05; "P<0.005;" "P<0.0005;" "P<0.0001. MBEC, minimum biofilm eradication concentration; FBEC, fractional biofilm eradication concentration, according to an embodiment.
Figure 5:
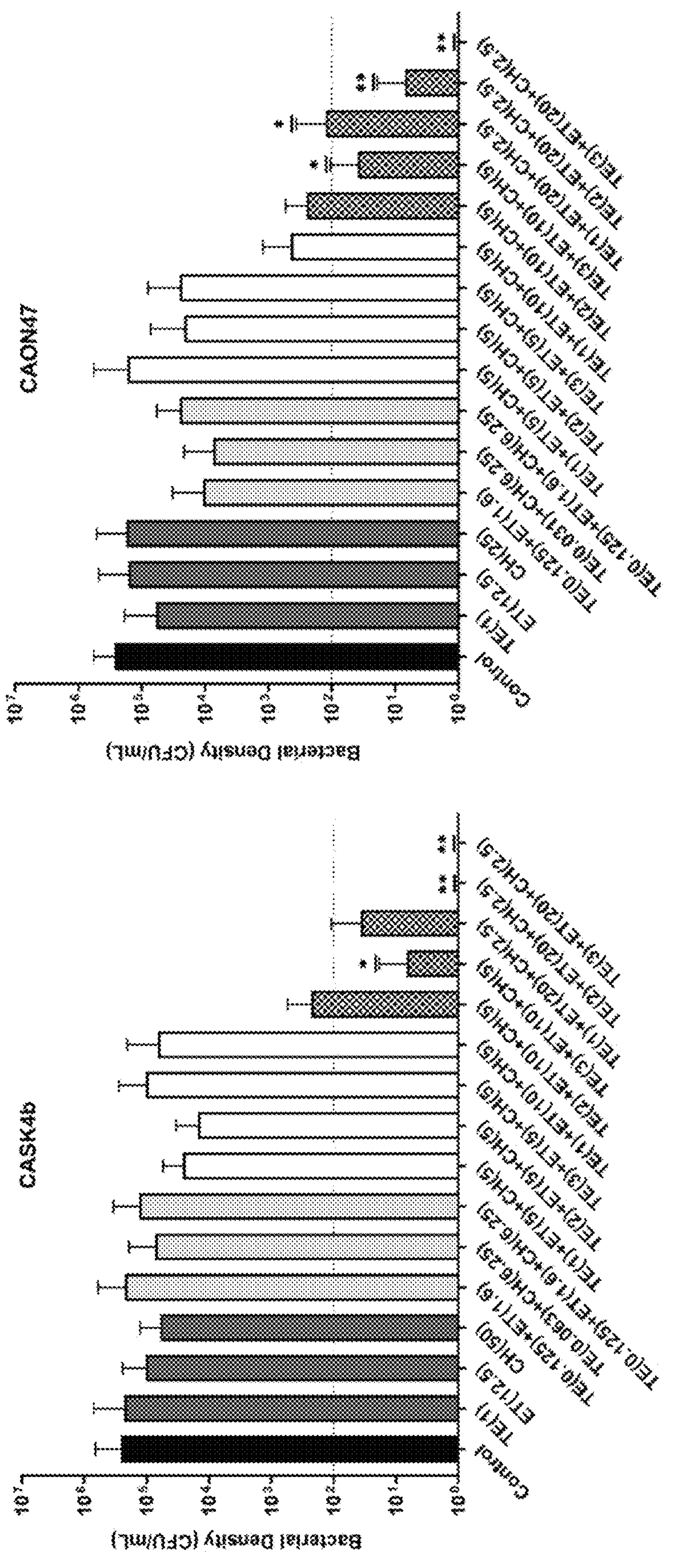
FIG. 5 is a graphical representation for the efficacy of tetrasodium EDTA (TE), ethanol (ET), and chlorhexidine HCl (CH) against fungal biofilms in a 2-hour exposure period. Each column represents different concentrations of test antimicrobials against each organism tested: (i) three dark grey columns represent treatment with the MBEC of TE (%), ET (%) and CH (μg/m L); (ii) three light grey column represents treatment with the FBEC of TE+ET, TE+CH, and TE+ET+CH; and (iii) white and hatched columns represent treatment with triple combinations of TE+ET+CH, with hatched bar combinations showing the best killing/sanitizing effects. Statistical significance was determined by comparison with non-treated biofilms (black bar) and is indicated as follows: •p<0.05; ••p<0.005. MBEC, minimum biofilm eradication concentration; FBEC, fractional biofilm eradication concentration, according to an embodiment.

Example 9: Rapid Biofilm Eradication Ability of Test Antimicrobials Alone and in Combination Against 48-h-Old Biofilms within 2 Hour Exposure Time This example demonstrates initially choosing different concentrations of test antimicrobials to assess their potency in eradicating preformed biofilms of study organisms within two hours. Then, secondly, evaluating the quantitative recovery from biofilms following exposure to the antimicrobial solutions for bacterial strains (FIG. 4) and fungal strains (FIG. 5). Then, (3) measuring the exposure to the MBEC of tetrasodium EDTA, ethanol, or chlorhexidine HCl alone as well as in several double and triple combinations of FBEC of antimicrobials failed to eradicate the preformed biofilms after two h of exposure. Then (4) all tested bacterial and fungal biofilms were entirely eradicated by the triple combination of 20% ethanol and 2.5 μg/mL chlorhexidine HCl in 3% tetrasodium EDTA (FIGS. 4 and 5).

A triple combination of 20% ethanol and 2.5 μg/mL chlorhexidine HCl in 2% tetrasodium EDTA ultimately killed all biofilm cells except for three strains (MRSA ON184, *P. mirabilis* ON153, and *C. albicans* SK4b), but even for these strains, the viable cells were significantly reduced to at or near the limit of detection. Likewise, a combination of 1% tetrasodium EDTA with 20% ethanol and 2.5 μg/mL chlorhexidine HCl significantly reduced the viable cells in six of eight test organisms in comparison with their respective controls. A triple combination of 3% tetrasodium EDTA with 10% ethanol and 5.0 g/mL chlorhexidine HCl also showed a significant reduction in viable biofilm cells of all test organisms within the 2-hour contact time.

Example 10: Other Compositions Derived from the Growing Concern Over Multidrug Resistance Among Pathogens This example demonstrates the combined with the increasing use of CVADs, have made it necessary to identify novel ALS to salvage long-term catheters. According to historical multi-institutional susceptibilities, empirical treatment for CLABS must include broad-spectrum antimicrobial agents expected to kill clinically essential pathogens. While some studies showed that combinations of antibiotics are more effective than single antibiotics, the efficacies of nonantibiotic antimicrobial agents are currently being investigated to reduce the risk of emerging resistance among clinically relevant pathogens. Combining antimicrobial agents that exhibit synergy, partial synergy, or even additive effects could decrease toxicity and enhance the overall treatment efficacy for severely ill patients, the use of EDTA as a sensitizing and potentiating agent.

Other compositions derived from several in vitro studies demonstrated that the biofilm-disrupting efficacy of EDTA is due to its ability to sequester metal cation ($Ca^{+2}$, $Fe^{+3}$, and $Mg^{+2}$) necessary for the biofilm matrix, thereby enhancing the killing effect of other antimicrobial agents. The combination of disodium EDTA with antibiotics and other antimicrobial agents has been widely studied since it increases combined drugs' antimicrobial potential against bacterial and fungal biofilms. A triple combination of minocycline (3 mg/mL), EDTA (30 mg/mL), and ethanol (25%) synergistically eradicated preformed biofilms of methicillin-resistant *S. aureus* (MRSA) and *Candida parapsilosis* on silicone catheters. The combination of chlorhexidine 0.15% with Tris-EDTA has shown excellent synergistic activity against *Pseudomonas* and all pathogens commonly involved in canine otitis. These experiments suggested that the combination of EDTA with either ethanol or chlorhexidine does not compromise the activity of one another. However, disodium EDTA or standard EDTA alone is not a potent antimicrobial agent (i.e., does not kill cells) even when used at high concentrations against a broad range of microbial species. During the last decade, tetrasodium EDTA has been proven for its broad-spectrum antimicrobial and antibiofilm properties; the KiteLock™ formulation was recently approved as a medical device in Canada. As reported, tetrasodium EDTA (40 mg/mL) locked for 21-25 h reduced biofilm colonization by *Klebsiella pneumoniae, E. coli, S. epidermidis, P. aeruginosa*, and *C. albicans* on catheter segments. This was in line with previous study wherein the reported biofilm eradication and microbial killing ability of 4% tetrasodium EDTA against clinically relevant pathogens. The evaluation in vitro antimicrobial efficacy of tetrasodium EDTA in combination with ethanol and chlorhexidine HCl against planktonic and sessile cells of bacterial and fungal pathogens to extend the range of efficacy for this group of compounds.

Other compounds derived from ethanol have been well studied for their antimicrobial potency as a standalone agent and in combination with other antimicrobials.

According to recent studies and global regulatory registries for disinfectants and antiseptics, a minimum of 60% ethanol is required to provide a 3-log reduction against commonly encountered pathogens. Reported adverse events with the use of high concentrations of ethanol, especially as an ALS for CVADs, include breaches in catheter integrity, systemic toxicity, and protein precipitation causing intraluminal occlusions. Although effective against bacteria, high concentrations of ethanol are not recommended for contact with open wounds and are also associated with an increased risk of flammability.

Other compositions that are derived from chlorhexidine (1,6-bis(4'-chlorophenylbisguanide(hexane)) are a divalent cationic biguanide agent that exists as acetate, gluconate, and hydrochloride salts. Chlorhexidine has been utilized for over 50 years in preparations for hand cleansing, both in general and pre-surgical events. Owing to its broad-spectrum antimicrobial activity with low mammalian toxicity and strong binding affinity on the skin, to date, it is one of the most frequently used antiseptics in clinical sectors. The combination of 2% chlorhexidine in 70% isopropyl alcohol solution was used to decontaminate catheter hubs, the insertion site as well as needle free devices before and after use. The use of chlorhexidine-impregnated CVADs has been found to reduce bacterial colonization and catheter-related infections. However, it has been widely recognized as a significant allergen in perioperative and clinical care settings and is also reported to cause chemical burns in infants. Furthermore, growing evidence of reduced susceptibility from its overuse and a cross-resistance to colistin further supports the need to find alternative and more efficient combination solutions to reduce avoidable selection pressure.

Other compositions derived from the results demonstrated that all test antimicrobials had efficient antimicrobial activity against planktonic and biofilm cells of test bacterial and fungal strains when exposed for 24 hours. The combination of tetrasodium EDTA and ethanol was synergistic against planktonic cells of 6 of 12 strains tested, as measured by fractional inhibitory concentration index (FICI) and fractional microbicidal concentration index (FMCI) activity. The interactions between tetrasodium EDTA and chlorhexidine HCl were categorized into synergistic, partially synergistic, additive, and indifferent activity against the test bacterial and fungal strains. It is noteworthy that there was no evidence of antagonistic activity between the three agents against planktonic cells in any tested combinations. We also tested the biofilm eradication ability of test antimicrobials against 48-hour old biofilms of bacterial and fungal strains within a 24-hour exposure; 4% tetrasodium EDTA, 50% ethanol, and 100 μg/mL chlorhexidine HCl alone were able to eradicate all established biofilms following 24 hours of treatment. As expected, for each organism, biofilm cells were more resistant than planktonic cells. When tetrasodium EDTA was combined with ethanol or chlorhexidine HCl and used to treat biofilms, these agents worked synergistically, showing a remarkable reduction in concentrations compared with the MBEC values of single test antimicrobials. In many cases, the concentration of each agent required was near or lower than the MICs measured against planktonic cells. This strongly indicated that these three antimicrobials could be successfully used together to kill pathogenic microbes.

Other compositions derived from successful combinations of antimicrobial agents show efficient microbicidal activity against organisms within a reasonable contact time. Based on the results obtained from previous studies and the present study, concentrations of all three agents were chosen to optimize the effective combinations to eradicate biofilms within a selected 2-h exposure. The present study demonstrated that triple combinations of either 3% tetrasodium EDTA with 10% ethanol and 5.0 μg/mL chlorhexidine HCl or of 3% tetrasodium EDTA with 20% ethanol and 2.5 μg/mL chlorhexidine HCl completely eradicated 48-hour old biofilms of all of the test organisms following a 2-hour exposure. In comparison with their individual antimicrobial effects, the combination of test antimicrobials significantly decreased the viable cells both of bacterial and fungal biofilms. The decrease in the ethanol concentration was compensated with an increased concentration of tetrasodium EDTA, and the effect was further accelerated with the addition of chlorhexidine HCl. The reduced ethanol concentration in the present study sets a more significant margin of safety from adverse reactions. In addition to improving safety, combination therapy may also decrease the risk of antimicrobial resistance among pathogens by reducing selection pressure. In addition, chlorhexidine concentrations above 2% have fewer human erythrocytes and neutrophils in vitro.

On the other hand, chlorhexidine at 0.2% did not induce cochlear or vestibular neurotoxicity when used in the ear canal with a perforated tympanic membrane in dogs. The toxicity of chlorhexidine is directly proportional to its concentration used. Considering the above facts, the concentration of chlorhexidine HCl used in the triple combination was 0.00025% in the present evaluation.

Other compositions derived from the combination of tetrasodium EDTA, ethanol, and chlorhexidine HCl demonstrated broad-spectrum antimicrobial activity on planktonic and biofilm cells of clinically relevant pathogens. Based on the biofilm eradication ability against the common CLABSI pathogens tested, this combination should be studied further through in vivo and clinical trials to establish its efficacy in treating CLABSIs. While investigating the synergistic use of all three compounds for use as an ALS, potential adverse effects might restrict the use of this combination of compounds to more topical applications, such as disinfecting skin surfaces at catheter insertion sites. It is also likely that specific combinations would be effective against more complex polymicrobial infections, such as wound or burn infections.

What is claimed is:

1. An aqueous composition comprising:

(a) about 3.0 wt % of tetrasodium ethylenediaminetetraacetic acid (TE);

(b) about 20.0 wt % of ethanol (ET); and, (c) about 2.5 g/mL of chlorhexidine (CH) or a salt thereof, wherein the composition eliminates more than 95% of biofilm cells after contacting the biofilm cells for at least 2 hours.

2. The composition of claim 1, wherein the composition is an aqueous solution.

3. The composition of claim 1, wherein the composition eliminates more than 95% of planktonic cells.

4. The composition of claim 1, wherein the composition eliminates more than 99% of planktonic cells.

5. The composition of claim 1, wherein the composition eliminates more than 99% of biofilm cells.

6. The composition of claim 1, wherein the biofilm cells comprise bacterial or fungal cells.

7. The composition of claim 1, wherein the composition eliminates more than 95% of sessile cells.

8. The composition of claim 1, wherein the composition eliminates more than 99% of sessile cells.

9. The composition of claim 1, wherein the composition eliminates biofilm cells comprising Gram-positive cells, Gram-negative cells, or a combination thereof.

10. The composition of claim 1, wherein the composition provides equivalent MBEC values of single test antimicrobials at substantially lower concentrations of antimicrobials.

11. The composition of claim 1, wherein the composition eliminates a 48-hour old biofilm after a 2-hour exposure.

12. The composition of claim 1, wherein the composition provides a substantial reduction in biofilm cells within a 2-hour contact time.

13. The composition of claim 1, wherein the composition provides a substantial reduction in biofilm cells within a 30-minute contact time.

14. The composition of claim 1, wherein the composition eliminates ≥75% of strains of planktonic cells.

15. The composition of claim 1, wherein the composition eliminates ≥95% of strains of planktonic cells.

16. The composition of claim 1, wherein the composition eliminates ≥99% of strains of planktonic cells.

17. The composition of claim 1, wherein the composition eliminates ≥75% of strains of biofilm cells.

18. The composition of claim 1, wherein the composition eliminates ≥95% of strains of biofilm cells.

19. The composition of claim 1, wherein the composition eliminates ≥99% of strains of biofilm cells.

20. The composition of claim 1, wherein the composition eliminates ≥99% biofilms following 24 hours of treatment or exposure.

21. An aqueous composition consisting of:

(a) about 3.0 wt % of tetrasodium ethylenediaminetetraacetic acid (TE);

(b) about 20.0 wt % of ethanol (ET);

(c) about 2.5 μg/mL of chlorhexidine (CH), a salt thereof, or a combination thereof; and (d) water, wherein the aqueous composition eliminates more than 95% of biofilm cells after contacting the biofilm cells for at least 2 hours.

* * * * *